United States Patent
Hikem et al.

(10) Patent No.: US 12,163,267 B2
(45) Date of Patent: *Dec. 10, 2024

(54) WASHING MACHINE INCLUDING A METERING APPARATUS FOR DISPENSING LAUNDRY FLUIDS AND METHODS FOR MAKING AND USING SAME

(71) Applicant: HIKETRON INC., Brookshire, TX (US)

(72) Inventors: Aziz Hikem, Katy, TX (US); Tara Lee Hikem, Katy, TX (US)

(73) Assignee: Hiketron Inc., Sealy, TX (US)

( * ) Notice: Subject to any disclaimer, the term of this patent is extended or adjusted under 35 U.S.C. 154(b) by 868 days.

This patent is subject to a terminal disclaimer.

(21) Appl. No.: 17/018,805

(22) Filed: Sep. 11, 2020

(65) Prior Publication Data
US 2021/0032091 A1  Feb. 4, 2021

Related U.S. Application Data

(62) Division of application No. 16/132,756, filed on Sep. 17, 2018, now Pat. No. 10,800,644.

(60) Provisional application No. 62/578,623, filed on Oct. 30, 2017, provisional application No. 62/558,991, filed on Sep. 15, 2017.

(51) Int. Cl.
| | |
|---|---|
| *B67D 7/02* | (2010.01) |
| *D06F 33/37* | (2020.01) |
| *D06F 39/02* | (2006.01) |
| *G16Z 99/00* | (2019.01) |
| *D06F 105/60* | (2020.01) |
| *G16H 20/10* | (2018.01) |

(52) U.S. Cl.
CPC .......... *D06F 33/37* (2020.02); *B67D 7/0227* (2013.01); *D06F 39/022* (2013.01); *G16Z 99/00* (2019.02); *D06F 2105/60* (2020.02); *G16H 20/10* (2018.01)

(58) Field of Classification Search
CPC .... D06F 39/022; D06F 33/37; D06F 2105/60; G16Z 99/00; B67D 7/0227; G16H 20/10
See application file for complete search history.

(56) References Cited

U.S. PATENT DOCUMENTS

| | | | | |
|---|---|---|---|---|
| 3,190,502 | A * | 6/1965 | Knibb | A45D 19/00 |
| | | | | 222/146.5 |
| 4,135,647 | A * | 1/1979 | Mascia | F04B 43/1253 |
| | | | | 222/211 |
| 4,162,745 | A * | 7/1979 | Anderson, Jr. | A01M 7/0089 |
| | | | | 134/168 R |
| 4,176,793 | A * | 12/1979 | Heinrich | B05B 12/00 |
| | | | | 222/144.5 |

(Continued)

FOREIGN PATENT DOCUMENTS

| | | |
|---|---|---|
| CN | 203997335 | 8/2014 |
| WO | 9951354 A1 | 10/1999 |

(Continued)

*Primary Examiner* — Benjamin L Osterhout
(74) *Attorney, Agent, or Firm* — Robert W. Strozier

(57) ABSTRACT

Apparatuses for dispensing household fluids including a handheld device or wand including a pump for dispensing one or more household fluids at a rate and for a time sufficient to dispense a pre-determined or variable amount of the fluids into an appliance, and to methods for making and using same.

8 Claims, 21 Drawing Sheets

(56) References Cited

U.S. PATENT DOCUMENTS

| | | | |
|---|---|---|---|
| 4,182,491 A * | 1/1980 | Parke | A01M 7/0089 239/11 |
| 4,618,099 A | 10/1986 | Nagao et al. | |
| 4,790,454 A * | 12/1988 | Clark | A01C 23/042 222/136 |
| 4,801,088 A * | 1/1989 | Baker | B05B 9/0861 239/152 |
| 4,925,105 A * | 5/1990 | Lin | B05B 9/0861 222/175 |
| 4,979,504 A | 12/1990 | Mills | |
| 5,014,884 A * | 5/1991 | Wunsch | B05B 9/0861 239/332 |
| 5,110,013 A * | 5/1992 | Clark | F16L 37/133 141/18 |
| 5,119,971 A | 6/1992 | Reyman | |
| 5,150,841 A * | 9/1992 | Silvenis | B05B 7/0018 137/512.4 |
| 5,165,558 A | 11/1992 | Cargile | |
| 5,188,259 A * | 2/1993 | Petit | B05C 17/0103 222/326 |
| 5,435,157 A * | 7/1995 | Laughlin | D06F 39/022 137/889 |
| 5,566,863 A * | 10/1996 | Mesenbring | B67D 1/0004 222/132 |
| 5,755,361 A * | 5/1998 | Restive | B05B 9/0883 222/209 |
| 5,938,116 A | 8/1999 | Restive et al. | |
| 5,988,435 A * | 11/1999 | Edwards | B67D 7/02 222/1 |
| 6,279,836 B1 * | 8/2001 | Toetschinger | B05B 7/2443 239/305 |
| 6,293,762 B1 * | 9/2001 | Farkhan | B29C 73/166 417/234 |
| 6,557,732 B2 | 5/2003 | Van Rompuy et al. | |
| 6,595,437 B1 * | 7/2003 | Lawson | A47L 9/244 239/119 |
| 6,685,056 B1 * | 2/2004 | Argentieri | B05B 9/0861 222/325 |
| 6,843,390 B1 * | 1/2005 | Bristor | B05B 11/3081 222/145.5 |
| 7,097,119 B2 | 8/2006 | Hornsby et al. | |
| 7,111,762 B2 * | 9/2006 | Saunders | G01F 11/029 222/333 |
| 7,513,444 B1 * | 4/2009 | Kurimski | E04D 15/07 215/286 |
| 7,588,198 B2 * | 9/2009 | Hornsby | B05B 9/0861 239/308 |
| 7,690,533 B2 | 4/2010 | Stilley | |
| 8,141,754 B2 | 3/2012 | Conner et al. | |
| 8,950,447 B2 | 2/2015 | De Rosa et al. | |
| 9,061,325 B2 | 6/2015 | West et al. | |
| 9,452,453 B2 * | 9/2016 | Buijsman | B05B 13/005 |
| 9,497,953 B2 | 11/2016 | Mitchell et al. | |
| 9,636,280 B1 | 5/2017 | Althallab | |
| 9,706,754 B2 * | 7/2017 | Prescott | A61M 5/2066 |
| 9,801,757 B2 * | 10/2017 | Voss | A61F 9/00 |
| 10,167,863 B1 * | 1/2019 | Cook | F04B 23/06 |
| 10,344,416 B2 * | 7/2019 | Rupnow | C11D 17/00 |
| 10,800,644 B2 * | 10/2020 | Hikem | G16Z 99/00 |
| 2003/0127110 A1 * | 7/2003 | Reichold | A47L 15/0081 134/25.2 |
| 2004/0011886 A1 | 1/2004 | Lawson et al. | |
| 2004/0118940 A1 * | 6/2004 | Lavitt | A01G 25/145 239/302 |
| 2008/0006717 A1 | 1/2008 | Junkel et al. | |
| 2008/0105701 A1 | 5/2008 | Niss et al. | |
| 2009/0095027 A1 * | 4/2009 | Deppermann | D06F 33/37 68/12.02 |
| 2011/0057436 A1 * | 3/2011 | Schrum | F16L 37/248 285/33 |
| 2011/0198413 A1 * | 8/2011 | Thompson | B05B 9/043 239/322 |
| 2012/0152290 A1 * | 6/2012 | Brosnan | D06F 39/022 134/115 R |
| 2013/0049969 A1 * | 2/2013 | Kappler | D06F 39/022 340/618 |
| 2013/0098450 A1 * | 4/2013 | Frantz | D06F 31/00 137/1 |
| 2014/0263729 A1 | 9/2014 | Stewart | |
| 2015/0050169 A1 * | 2/2015 | Horie | B08B 3/026 417/410.1 |
| 2015/0258558 A1 | 9/2015 | Schrum et al. | |
| 2015/0283570 A1 | 10/2015 | West et al. | |
| 2016/0016778 A1 * | 1/2016 | Taylor | B67D 1/10 222/333 |
| 2017/0037559 A1 * | 2/2017 | Gallagher | D06F 39/022 |
| 2017/0202411 A1 | 7/2017 | Bouton | |
| 2018/0334770 A1 * | 11/2018 | Irabatti | D06F 37/12 |
| 2019/0092616 A1 * | 3/2019 | Hikem | B67D 7/0227 |

FOREIGN PATENT DOCUMENTS

| | | |
|---|---|---|
| WO | 0055052 A2 | 9/2000 |
| WO | 2006020903 A2 | 2/2006 |
| WO | 2010075506 A1 | 7/2010 |

* cited by examiner

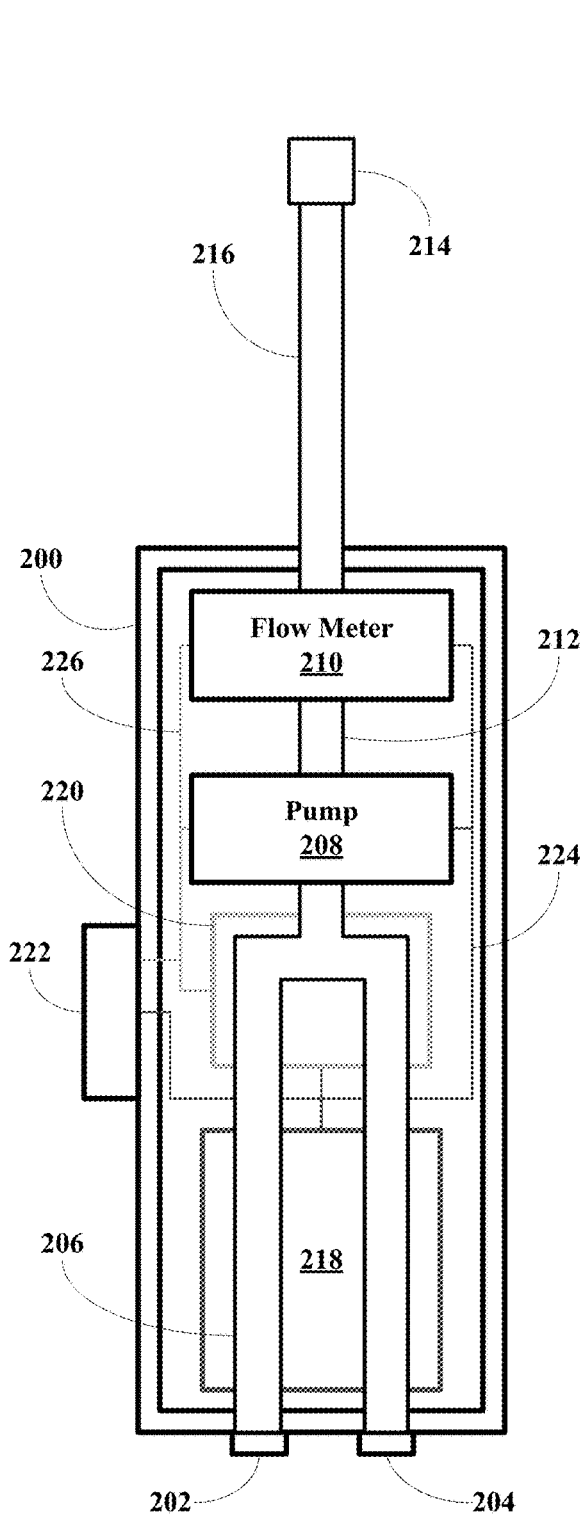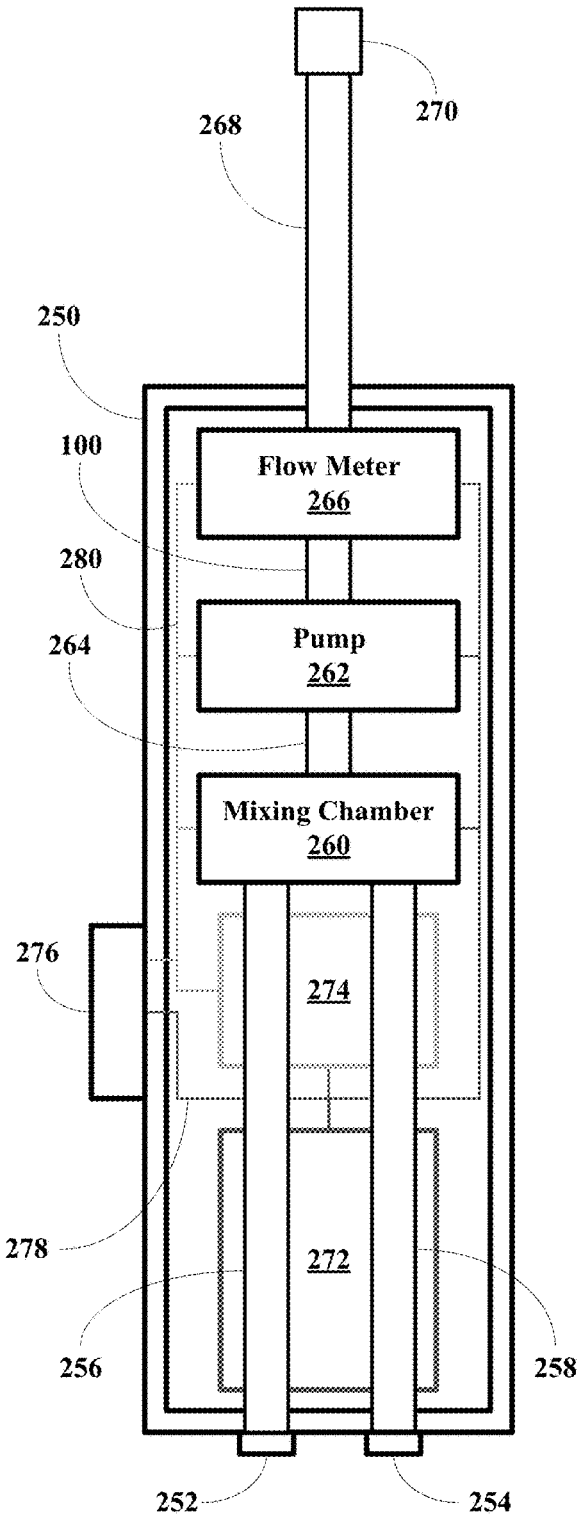

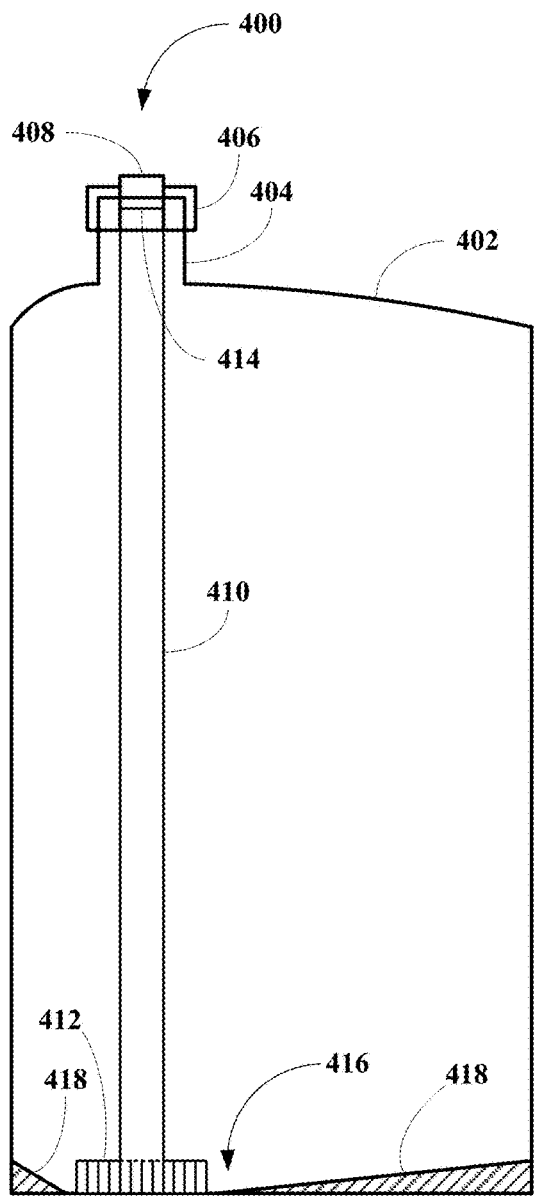
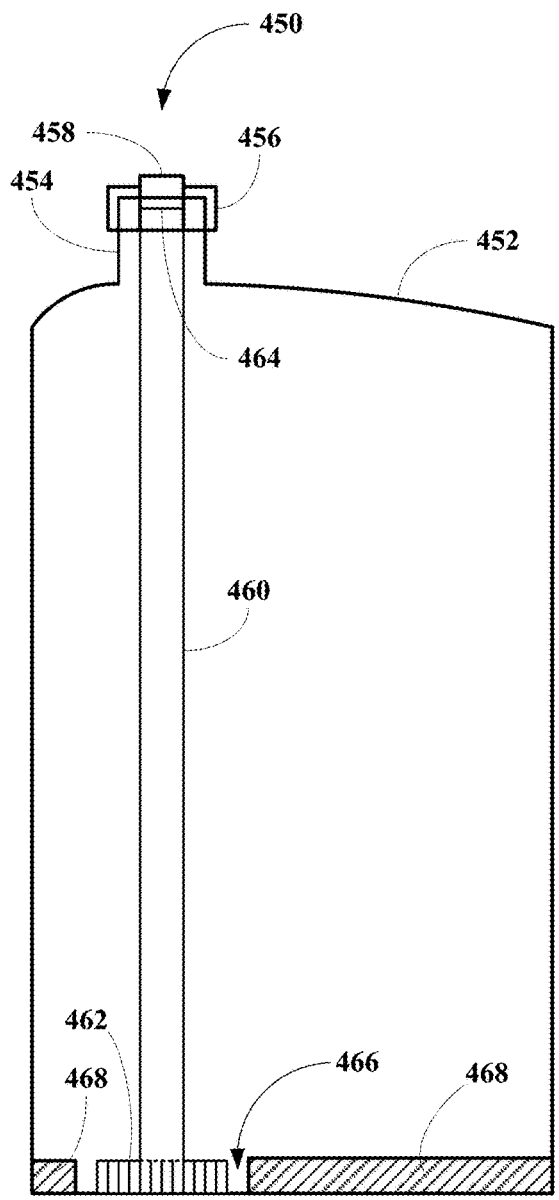
FIG. 4A  FIG. 4B

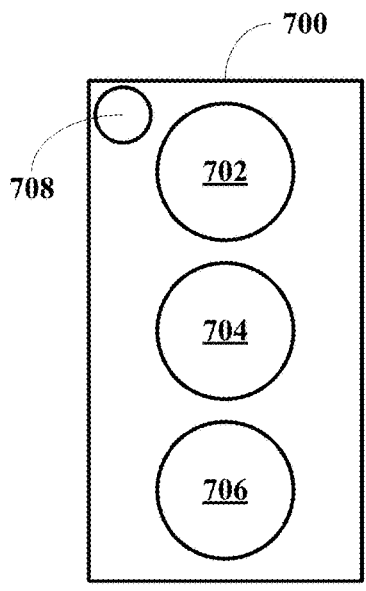 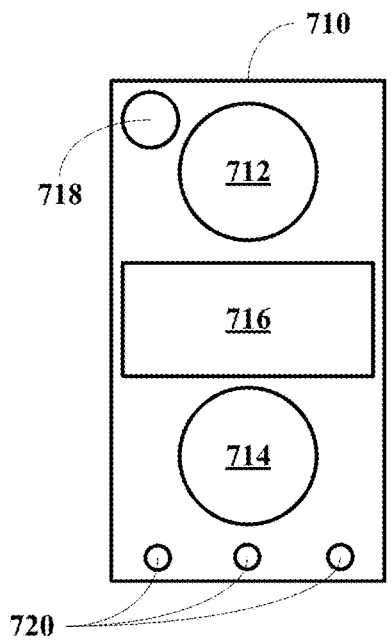 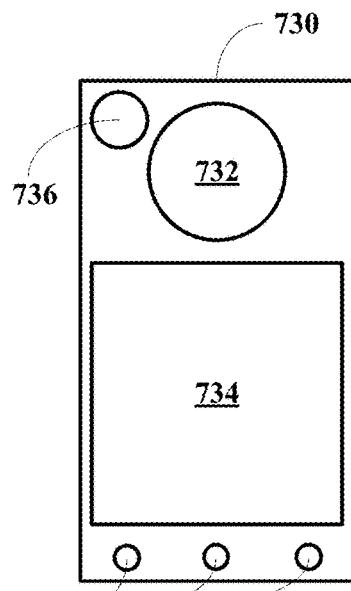
FIG. 7A    FIG. 7B    FIG. 7C
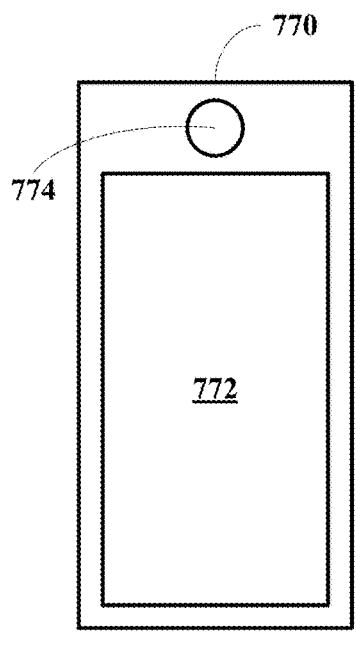 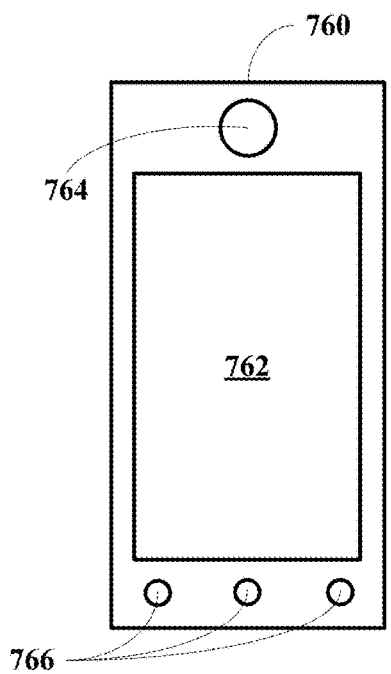 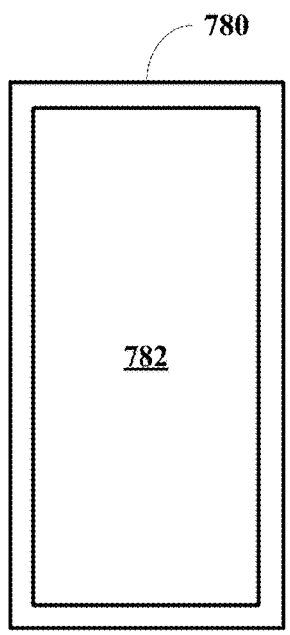
FIG. 7D    FIG. 7E    FIG. 7F

FIG. 12A  FIG. 12B

WASHING MACHINE INCLUDING A METERING APPARATUS FOR DISPENSING LAUNDRY FLUIDS AND METHODS FOR MAKING AND USING SAME

RELATED APPLICATIONS

This application is a divisional application of U.S. patent application Ser. No. 16/132,756 filed Sep. 17, 2018 (17 Sep. 2018), which claims the benefit of and priority to U.S. Provisional Patent Application Ser. Nos. 62/558,991 filed 15 Sep. 2017 (Sep. 15, 2017) and 62/578,623 filed 30 Oct. 2017 (Oct. 30, 2017).

BACKGROUND OF THE DISCLOSURE

1. Field of the Disclosure

Embodiments of the present disclosure relate to apparatuses for dispensing a household fluid including a handheld device or wand or a dispensing unit and a handheld device or wand, and to methods for making and using same.

In particular, embodiments of the present disclosure relate to apparatuses for dispensing laundry detergent including a handheld device or wand including a pump or a dispensing unit including a pump and a wand for dispensing a household fluid at a rate and for a time sufficient to dispense a pre-determined or variable amount of the fluid to a household appliance, and to methods for making and using same.

2. Description of the Related Art

The problem with the current bottles is their weights once full and the complexity of handling them especially for people with disabilities, senior citizens and even normal people.

Most bottles with dispensing spouts are messy and not accurate in dispensing the liquids even though most bottles come with measuring cups, but only for one load. Some bottles are clear so you can see how much product is left, but most of the bottles are made with solid colors so you can't see how much product is left.

Deepening bleach is also a big issue, because it's a hazardous material and its affect on color when in contact with clothes.

Dispensing laundry detergent is a sloppy business. Often times users are faced with spillages, dispensing inconsistent amounts of detergent for each wash, or dispensing more or less than manufacturers recommended amount of detergent for a given load of laundry for a given machine.

Consumers don't feel fully in control when using/dosing current laundry detergent, fabric softener or any other big volume household products. Most current packages are not Intuitive to dose the correct amount; they are messy and not easy to handle and most importantly they are not flexible or adjustable to dose different volumes for varying jobs. Most consumers have difficulties in dispensing these products and usually end up overdosing them.

In addition to the lack of control, it appears that too much waste is generated in current packages and there is always product left behind or more often difficult to get out.

Consumers feel disconnected from the manufacturers of household products they use every day despite a massive social media presence.

The problem has been addressed by making smaller bottles and more lightweight bottles with different shapes and construction materials. The problem with smaller bottles is cost per ounce is high and the frequency of purchasing the product is high.

Another solution was to create a washing machines with integrated reservoirs to be filled with liquids and to be dispensed internally just like water. The issue is that this technology has some limitations because of the moving parts of the washing machine and even if this model will become popular it will take many years before all the existing washing machines will be converted.

Blending concentrated products also has been offered as another way to minimize cost and save storage space. The issue with this method is that most products are too thick and they present challenges in their manufacturing process and they do not dissolve as good.

Others offered combined products such as softener and laundry detergent. The issue with these products is that they are not as effective as if they are dispensed separately because of their competing and incompatible chemistries. Most softeners are usually acidic in nature and most laundry detergent is basic in nature.

While many apparatuses and methods have been purposed for controlling the amount of household fluid dispensed from a household fluid container into a household appliance prior to running the appliance, there is still a need in the art for improved systems and methods for dispensing household fluid to household appliances

SUMMARY OF THE DISCLOSURE

Embodiments of this disclosure provide apparatuses including at least one cap for engaging at least one container, where one container contains a household fluid, having a dip tube, a handheld fluid metering device or a wand including a microprocessing unit having wireless communication hardware and software, a pump, optionally a flow meter, optionally a flow controller, a power supply, at one fluid inlet, a fluid outlet, at least one fluid conduit, and a control unit, where the processing unit, the pump, the optional flow meter, the optional flow controller, the control unit, and the power supply are in electrical communication and where the pump and the flow meter are under the control of the processing unit. In certain embodiments, the apparatuses include at least two caps having a dip tube and the wand further includes a mixing chamber for mixing at least two fluids together prior to being pumped through the pump and out the outlet. In certain embodiments, the household fluid is a laundry detergent. In other embodiments, one of the household fluids is a laundry detergent and another of the household fluids is water. In other embodiments, one of the household fluids is a laundry detergent, one of the household fluids is water and one of the household fluids is fabric softener, a stain removing fluid, a bleaching fluid, any other fluid used for washing clothes, or mixtures thereof.

Embodiments of this disclosure provide methods for dispensing at least one household fluid including receiving a first input from a control unit of a handheld unit associated with a household fluid dispensing apparatus of this disclosure, turning on a pump of the handheld unit, and dispensing a specific amount of the fluid into a household appliance. The methods may also include receiving a second input from the control unit corresponding to selecting the specific amount. The methods may also include outputting a signal corresponding to an amount of fluid remaining a container containing the fluid from which the fluid is dispensed. The methods also include pulling information from a website associated with the fluid to set the specific amount of fluid to be dispensed to the appliance.

Embodiments of this disclosure provide apparatuses including a dispensing unit comprising a household fluid compartment containing a household fluid and a dip tube, a handheld fluid metering device or a wand including a microprocessing unit or a microprocessor or a processor having wireless communication hardware and software, a pump, optionally a flow meter, optionally a flow controller, a power supply, at one fluid inlet, a fluid outlet, at least one fluid conduit, and a control unit, where the processing unit, the pump, the optional flow meter, the optional flow controller, the control unit, and the power supply are in electrical communication and where the pump and the flow meter are under the control of the processing unit. In certain embodiments, the apparatuses include at least two caps having a dip tube and the wand further includes a mixing chamber for mixing at least two fluids together prior to being pumped through the pump and out the outlet. In certain embodiments, the household fluid is a laundry detergent. In other embodiments, one of the household fluids is a laundry detergent and another of the household fluids is water. In other embodiments, one of the household fluids is a laundry detergent, one of the household fluids is water and one of the household fluids is fabric softener, a stain removing fluid, a bleaching fluid, any other fluid used for washing clothes, or mixtures thereof.

Embodiments of this disclosure provide methods for dispensing at least one household fluid including receiving a first input from a control unit of a handheld unit associated with a household fluid dispensing apparatus of this disclosure, turning on a pump of the handheld unit, and dispensing a specific amount of the fluid into a household appliance. The methods may also include receiving a second input from the control unit corresponding to selecting the specific amount. The methods may also include outputting a signal corresponding to an amount of fluid remaining a container containing the fluid from which the fluid is dispensed. The methods also include pulling information from a website associated with the fluid to set the specific amount of fluid to be dispensed to the appliance.

Embodiments of this disclosure provide apparatuses include a washing machine including a dispensing unit of this disclosure. Embodiments of this disclosure also provide methods for using the washing machines including a dispensing unit of this disclosure.

Embodiments of this disclosure provide apparatuses include a plurality of washing machines, each including a control panel and three fluid inlets so receiving one or three different fluids. The apparatuses also include a dispensing unit including three reservoirs, three different pump and flow controllers, three different conduits, a power supply, and a processor, where commands entered at a washing machine are transmitted to the processor that then dispensing the indicated fluids and amounts.

Embodiments of this disclosure provide methods for dispensing fluid to a plurality of washing machines in a laundry mat.

Embodiments of the apparatuses may also include a concierge button, where a customer is able to push a button or invoke a command to be connected to customer service to handle issues that may arise from using the apparatuses and methods disclosed herein.

Embodiments of the apparatuses and methods may also include a human cognizable feedback unit such as speakers or other audio devices, a display, or other audio visual devices so that customers may listen to music, watch TV or play video games while doing laundry or other household or commercial tasks.

Embodiments of the apparatuses and methods may also include realtime or substantially realtime sensors designed to alert consumers of low fluid levels so the re-ordering of product may be stream-lined and automated making re-ordering product less of a hassle. In other embodiments, the apparatus may have the capability for automated reordering, manually reordering, or ordering product on a pre-defined basis.

Embodiments of the apparatuses and methods may also include cartridges (containers) for ease of product replacement. On demand inventory control facilitated by the communication of the devices with company headquarters, which may result in consumer savings and increase economical use of household fluids as the apparatuses described herein increase fluid usage and fluid level monitoring.

Embodiments of the present disclosure may also relate to products exclusively tailored for use in the apparatuses described herein.

Embodiments of the present disclosure may also include apparatuses, systems, and methods that are adapted to collect fees for using of fluids in such settings as laundry mats. The fees may be collected using coin devices well known the art or by using credit card or bank withdrawal devices also well known in the art. In this way, the apparatuses and systems may be fully automated in locations, where the general public may utilize apparatuses incorporating the dispensing apparatuses of this disclosure, so that fees may be easily collected for dispensing fluids without having the consumer bring their own or having to purchase fluid or powders that may be added to the washing machines.

BRIEF DESCRIPTION OF THE DRAWINGS OF THIS DISCLOSURE

The disclosure can be better understood with reference to the following detailed description together with the appended illustrative drawings in which like elements are numbered the same:

FIG. 2A depicts another embodiment of a wand of this disclosure, where the wand includes a pump, a flow meter, a microprocessor, and a power supply and capable of dispensing two fluids.

FIG. 2B depicts another embodiment of a wand of this disclosure, where the wand includes a mixing chamber, a pump, a flow meter, a microprocessor, and a power supply and capable of dispensing two fluids.

FIG. 4A depicts another embodiment of a designed container of this disclosure.

FIG. 4B depicts another embodiment of a designed container of this disclosure.

FIG. 7A depicts an embodiment of the control unit including buttons and a speaker.

FIG. 7B depicts another embodiment of the control unit including buttons, a slider, a speaker, and LEDs.

FIG. 7C depicts another embodiment of the control unit including buttons, a display, a speaker, and LEDs.

FIG. 7D depicts another embodiment of the control unit including a display and a speaker.

FIG. 7E depicts another embodiment of the control unit including a display, a speaker, and LEDs.

FIG. 7F depicts another embodiment of the control unit including a display.

Figure 12:
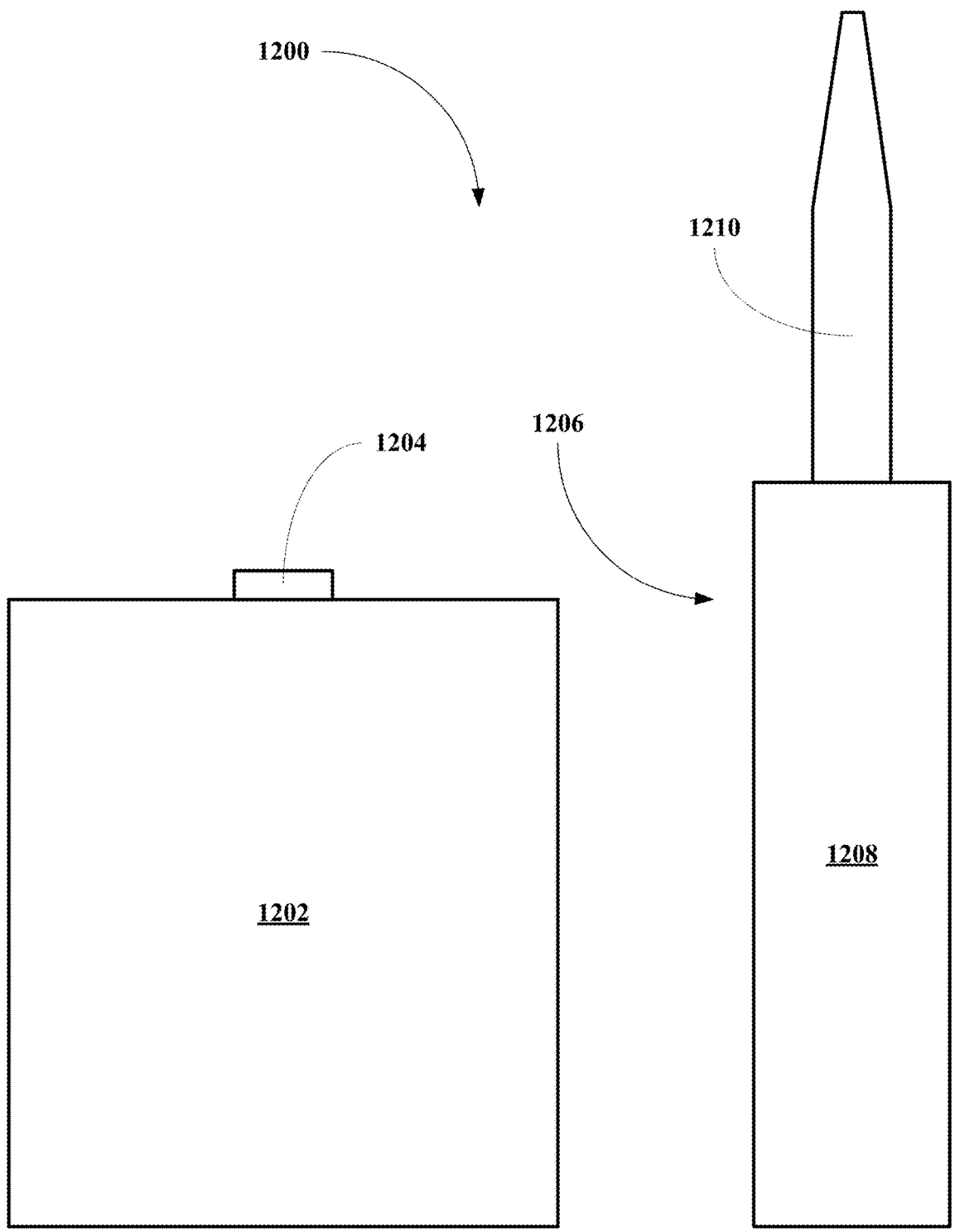

FIGS. 12A&B depicts another embodiment of a fluid dispensing apparatus of this disclosure, where the apparatus includes three fluid reservoir and a pipette.

Figure 13:
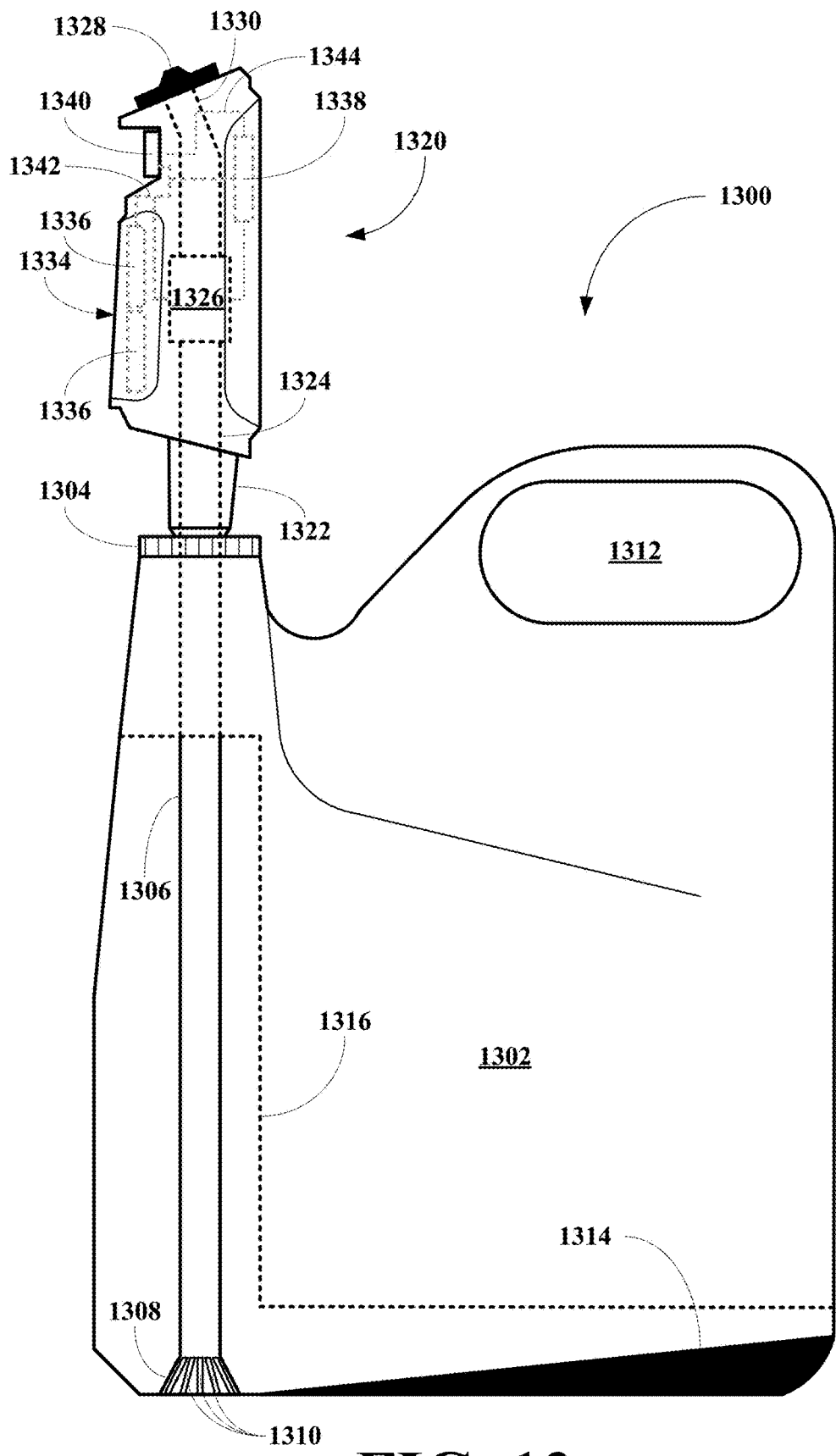

FIG. 13 depicts another embodiment of a fluid dispensing apparatus of this disclosure including a single fluid container.

Figure 14:
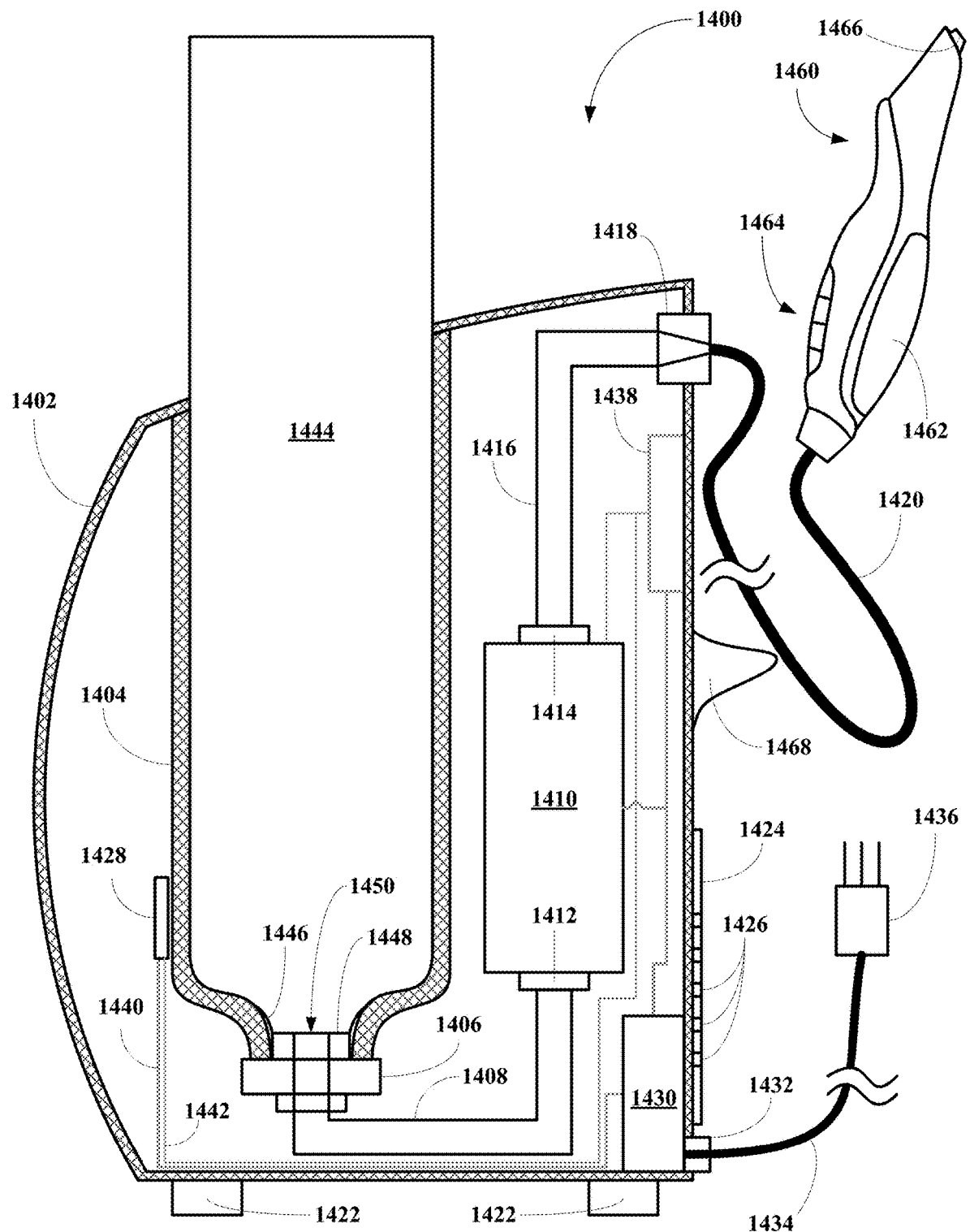

FIG. 14 depicts another embodiment of a fluid dispensing apparatus of this disclosure including a single fluid container.

Figure 15:
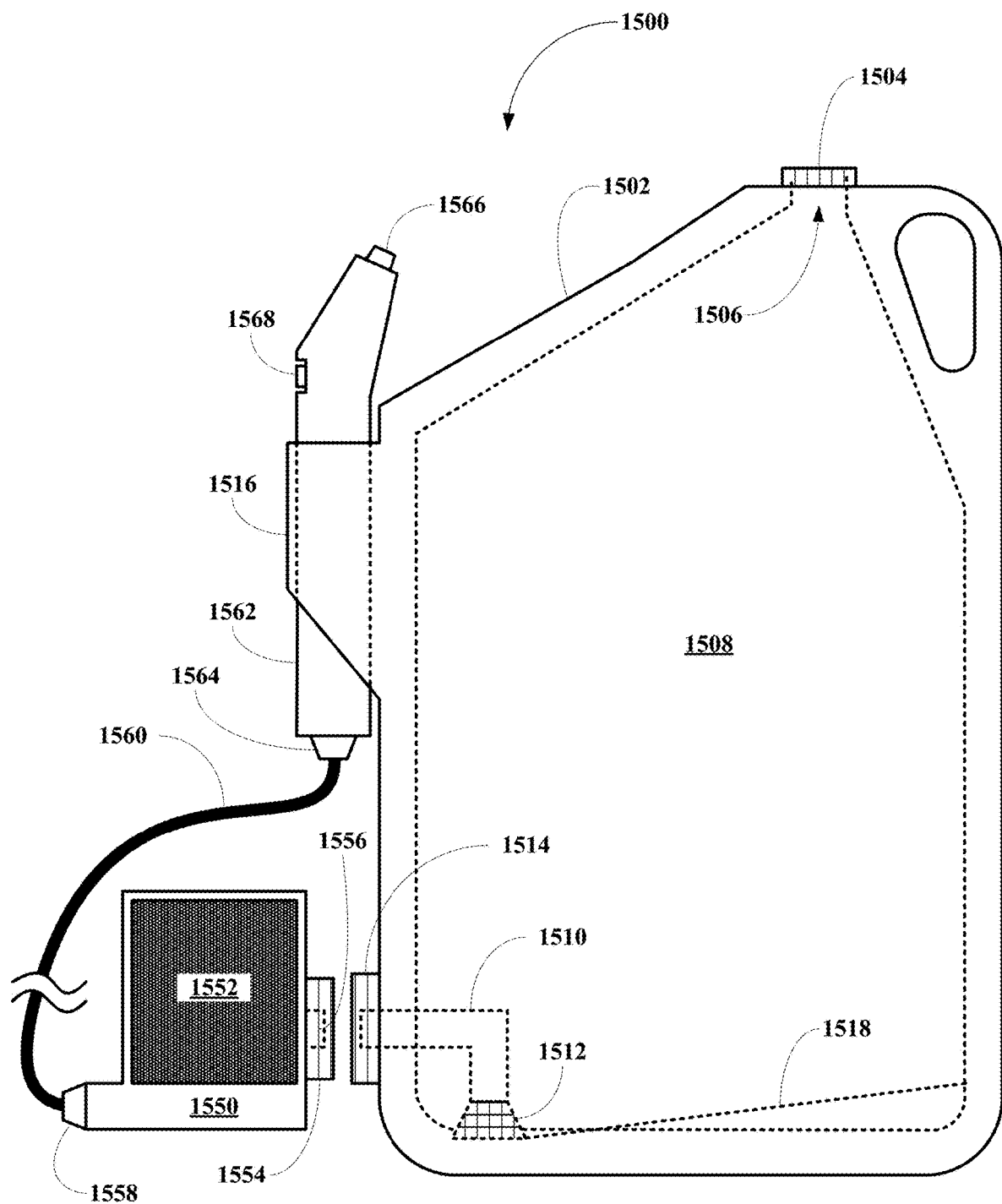

FIG. 15 depicts another embodiment of a fluid dispensing apparatus of this disclosure including a single fluid container.

Figure 16:
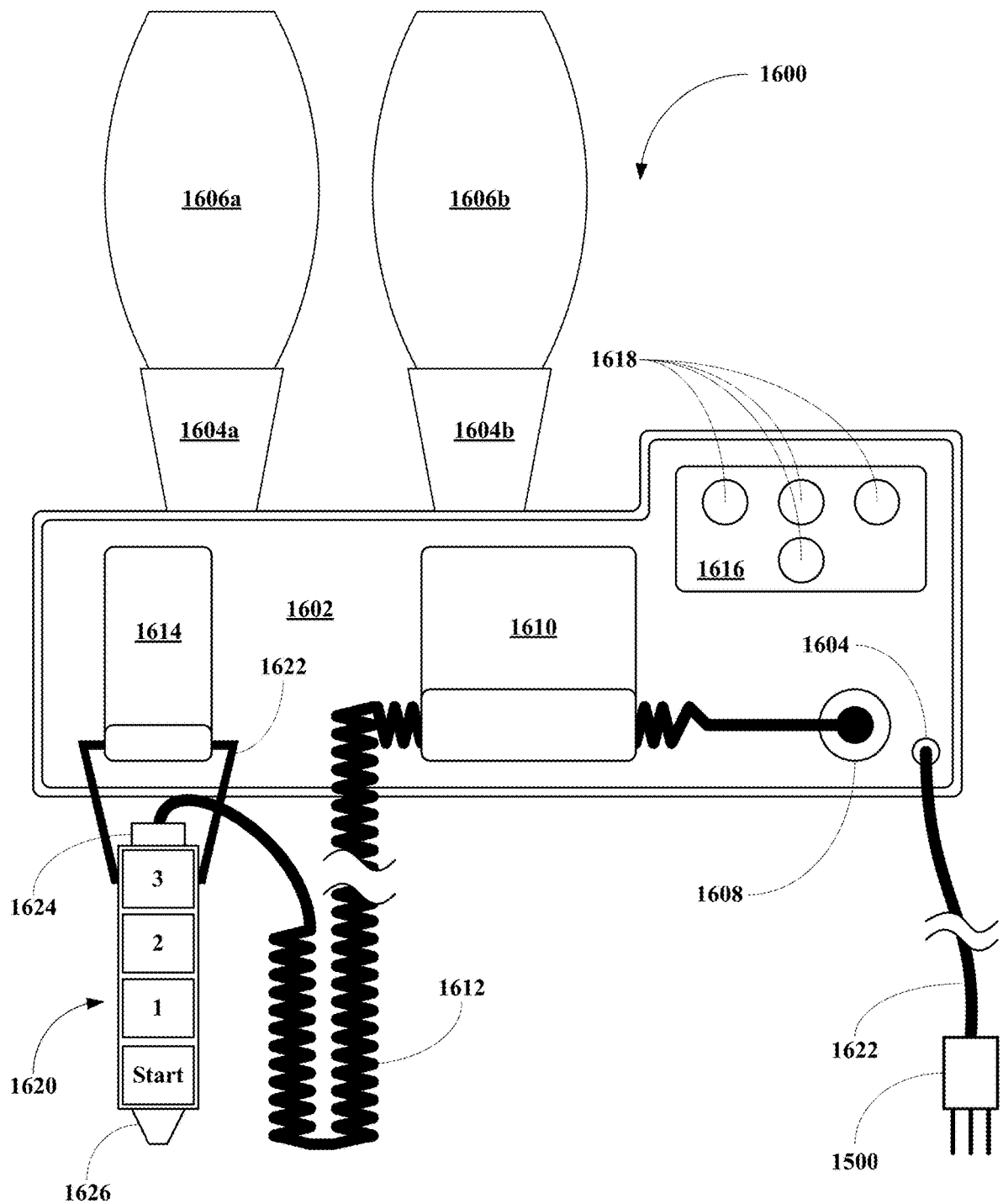

FIG. 16 depicts another embodiment of a fluid dispensing apparatus of this disclosure including two fluid containers.

Figure 17A:
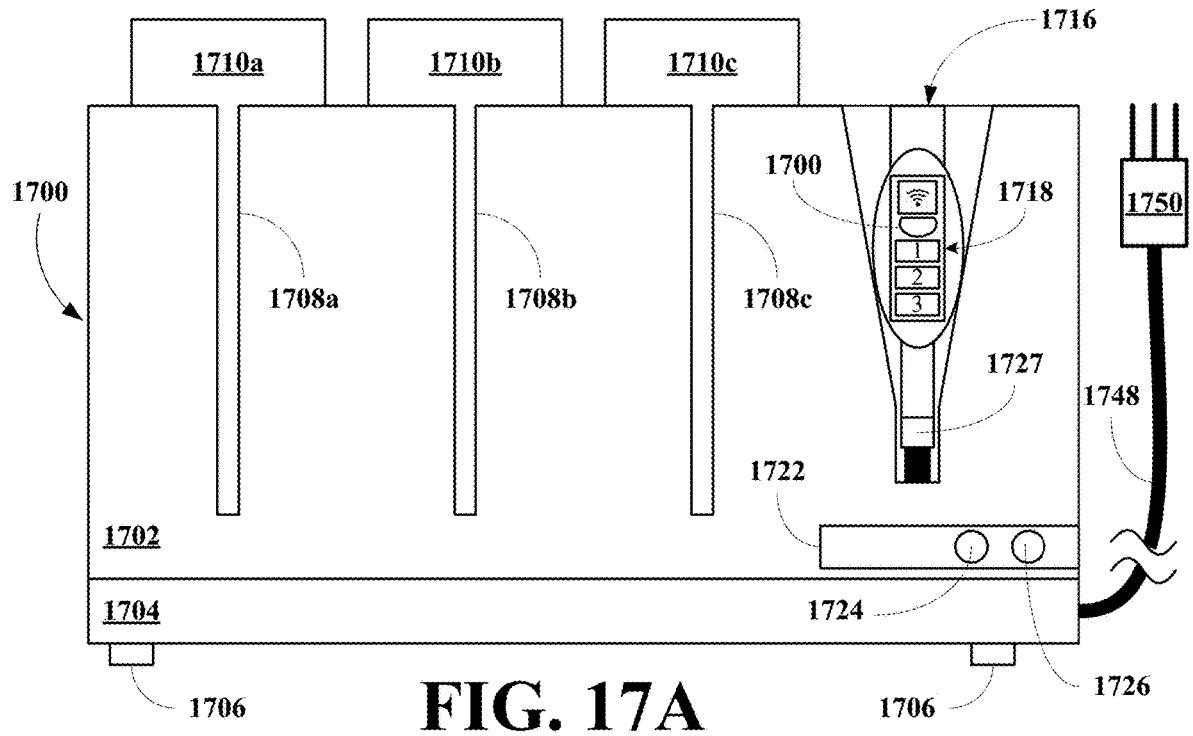

FIGS. 17A&B depict another embodiment of a fluid dispensing apparatus of this disclosure including three containers.

Figure 18:
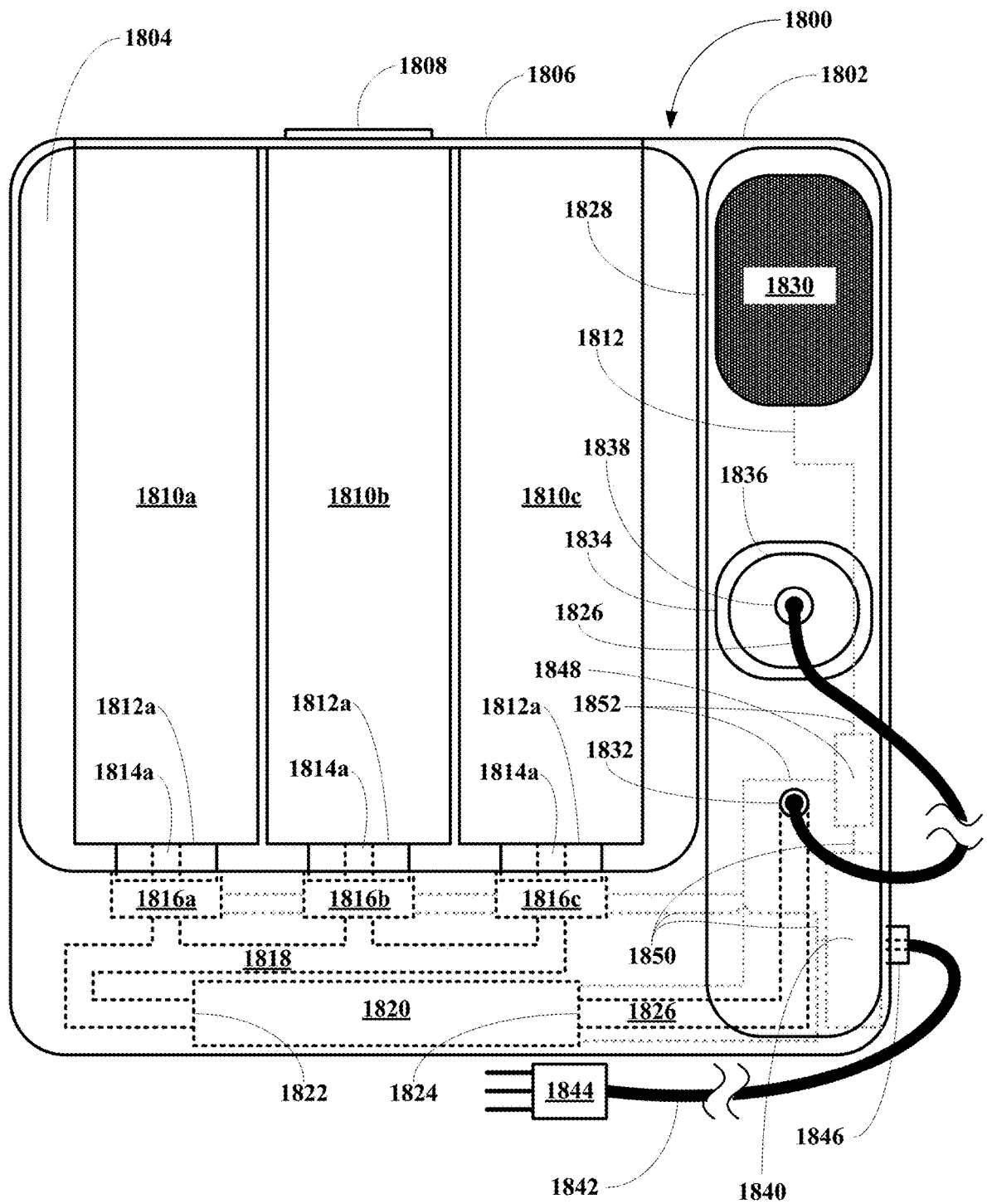

FIG. 18 depicts another embodiment of a fluid dispensing apparatus of this disclosure including three containers.

Figure 19:
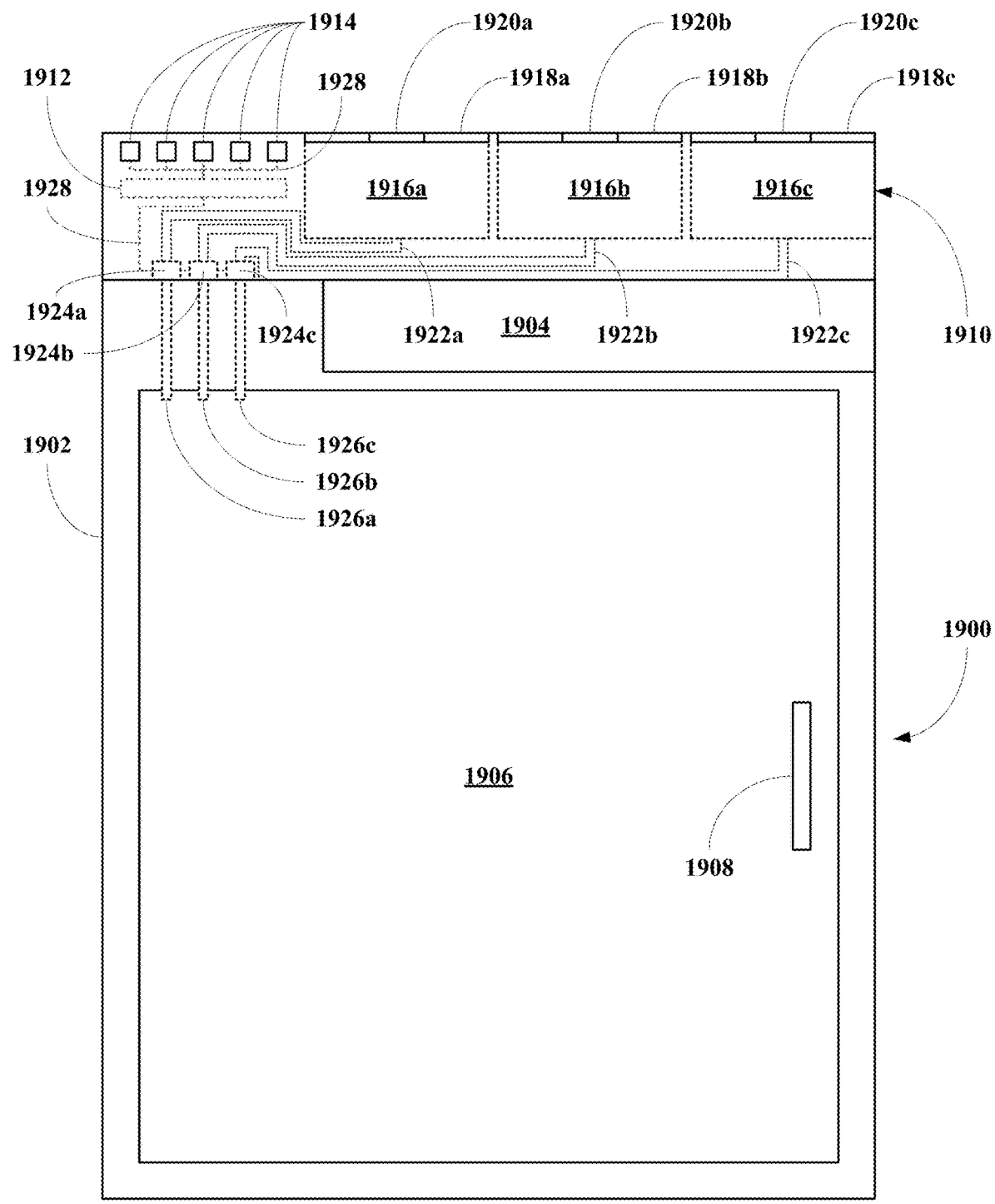

FIG. 19 depicts an embodiment of a washing machine apparatus including a fluid dispensing apparatus of this disclosure including three containers.

Figure 20A:
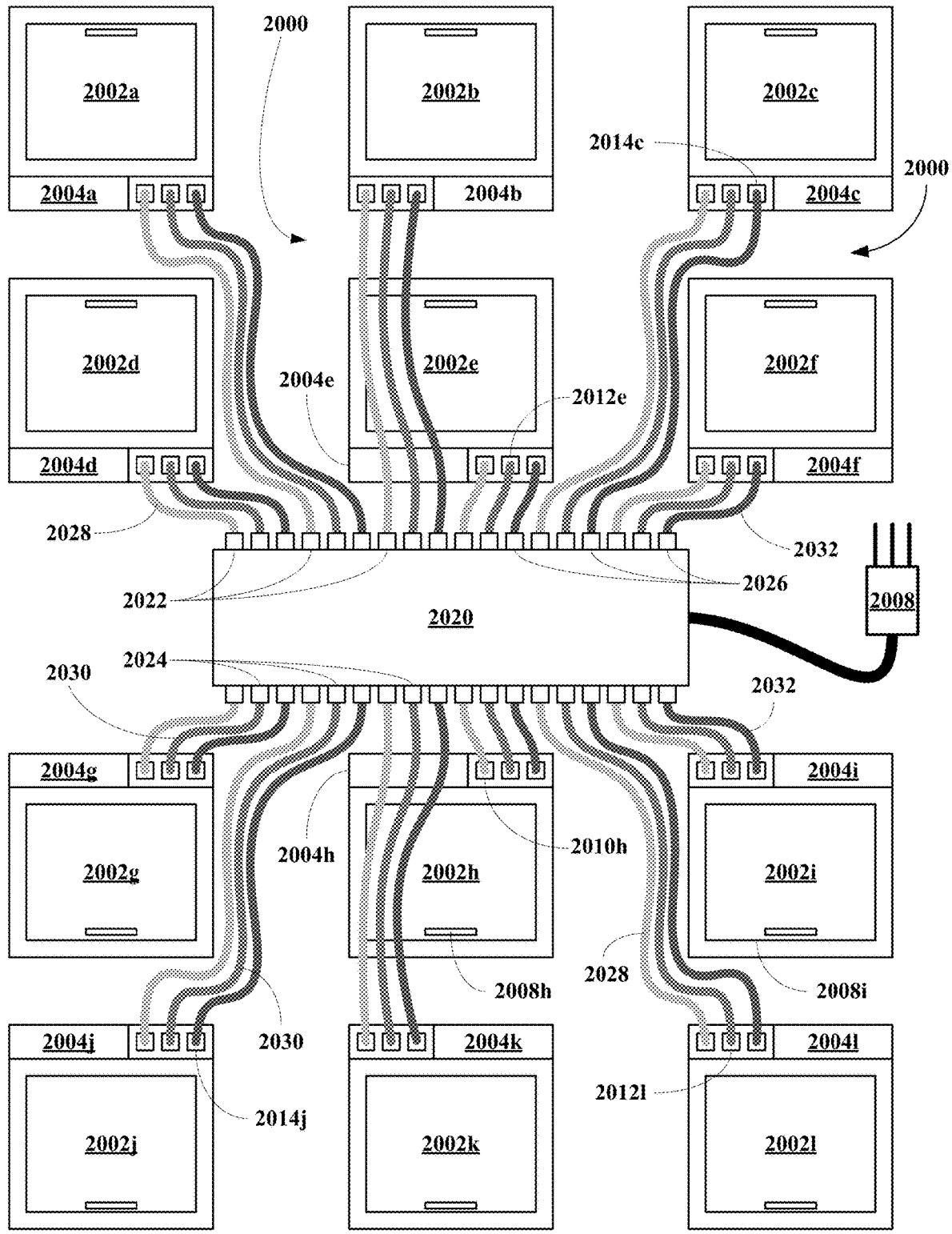

FIGS. 20A&B depict an embodiment of a washing machine fluid dispensing apparatus of this disclosure including three containers.

DEFINITIONS USED IN THE DISCLOSURE

In addition to having their customary and usual meaning, the following definitions apply where the context permits in the specification and claims:

The term "at least one" means one or more or one or a plurality, additionally, these three terms may be used interchangeably within this application. For example, at least one device means one or more devices or one device and a plurality of devices.

The term "one or a plurality" means one item or a plurality of items.

The term "about" means that a value of a given quantity is within ±20% of the stated value. In other embodiments, the value is within ±15% of the stated value. In other embodiments, the value is within ±10% of the stated value. In other embodiments, the value is within ±5% of the stated value. In other embodiments, the value is within ±2.5% of the stated value. In other embodiments, the value is within ±1% of the stated value.

The term "substantially" or "essentially" means that a value of a given quantity is within ±5% of the stated value. In other embodiments, the value is within ±2.5% of the stated value. In other embodiments, the value is within ±2% of the stated value. In other embodiments, the value is within ±1% of the stated value. In other embodiments, the value is within ±0.1% of the stated value.

DETAILED DESCRIPTION OF THE DISCLOSURE

The inventors have found that apparatuses for dispensing a household or industrial fluid or a plurality of household or industrial fluids may be constructed that includes a container having a cap including a dip tube, a wand or handheld device and a flexible fluid conduit interconnecting the dip tube and the wand, where the wand meters a controlled, pre-set or variable amount of the household or industrial fluid or fluids into a household appliance or industrial equipment and tracks the amount of fluid or fluids dispensed. The apparatuses are designed to simplify the dispensing of household or industrial fluid to a household appliance or industrial equipment, to control the amount of fluid or fluids supplied, and to track the amount of fluid used so that the wand may advice the user when the fluid or fluids container is low and needs to be replaced and/or refilled. The apparatuses are designed to improve the dispensing of a household appliance or industrial equipment fluids such as liquid detergents, liquid fabric softeners, liquid stain removers, liquid bleach, liquid bleach alternatives, and/or any other household fluid or any industrial fluid. The package includes a new bottle design and a battery-operated wand having a microprocessing unit or microprocessor having wireless hardware and software. Of course, it should be recognized that the processing unit or processor may be of any size including those used by traditional desktop and tap top computers.

The package also has a pump and flow meters for dispensing controlled, pre-set or variable amount of one or more household appliance or industrial equipment fluids. The wand may be connected to the bottle via a cap having unique threads, which cannot be used on any other bottles than the bottles described in this disclosure. The wand is designed to improve delivery of the household appliance or industrial equipment fluids. The processors include software or software applications to track usage and alert a consumer when it is time to replace, reorder, or refill associated containers or refill container with appropriate product. The application may also send reminders, offers, and discounts for the fluids and adjust amounts based on manufacturing recommendations. Additionally, for wands that dispense two or more (a plurality) household or industrial equipment fluids, the apparatuses may be capable of controlling the amount of each fluid and optionally mix them together prior to dispensing the mixed fluid.

The wand is designed to be purchased only once along with a laundry fluid container. Once the first bottle is empty, the consumer may buy additional fluid in a replacement container or a larger container and refill the existing container. In one embodiment, each fluid may have its own container and wand.

In other embodiments, the wand includes two or more fluid conduits, flow meters, flow controllers and an optionally a mixing chamber for mixing two or more fluids prior to the mixed fluid being dispensed. In other embodiments, the apparatuses include a multiple compartment container and a wand for each compartment, where each wand dispenses its corresponding fluid. In other embodiments, the apparatuses include a multiple compartment container and a wand having multiple fluid conduits, a fluid meter, multiple flow controllers, and an optionally a mixing chamber for mixing multiple fluids from some or all of the compartments prior to dispensing the mixed fluid.

The inventors have also found that the fluid dispensing apparatuses and methods of this disclosure have the advantage of making the dispensing of household fluids easier, cleaner, and more accurate. The controlled metering of household fluids represents distinct advantages over simply pouring fluids from containers. The present dispensing apparatus may also be used to determine the amount of fluid being poured out of a container, or changing the amount of fluids being dispensed depending on load size and changing recommendations on amounts. In fact, the controller and microprocessor used in the present apparatuses may be configured to receive information from the washing machine or other household appliance concerning such things as load size, load dirt content, floor dirtiness, or other factors that would affect the amounts and types of fluids being dispensed. Thus, if the apparatuses are dispensing laundry fluids, then information from the washing machine (either from sensor or from user input) may be used to control the amounts, types and timing of fluids being dispensed. If the apparatuses include detergent, softeners, and stain removers, then the information may be used to control the amounts of each fluid being dispensed, the timing of the fluid being dispenses, and whether the fluid are better dispensed mixed or unmixed, especially if the apparatuses are integrated into the washing machine.

The inventors also believe that apparatuses and methods of this disclosure provide the consumer with improved product control when using/dosing the product for the following reasons: (1) the present systems are intuitive to dose the correct amount for the job to be done, (2) the present systems are less messing, mess-free, or substantially mess-free, (3) the present systems are easy to handle and use, (4) the present systems are flexible or adjustable to dose different volumes for varying jobs, and (5) the present system are accurate and in control to avoid overdosing and minimizing waste and spillage. The present systems generate reduced waste, no waste or substantially no waste, use all or substantially all of the product, are easy to empty, minimize packaging waste and minimize overdosing or over use of products. The present systems allow complete and direct access to consumer to real-time or substantially real-time tracking of fluid usage. The present systems also allow Wi-Fi compatible or other wireless communication protocols and fully control of the apparatuses from a downloadable computer/phone app that tracks fluid usage. The present systems also allow consumers to be notified when it is time to reorder fluids and make reordering fluids easier such as a one click ordering methodology permitting the product to be delivered directly to the consumer's house or place of business. The downloadable app may also allow the user to access useful information on how to use the fluids effectively and efficiently.

Embodiments of this disclosure provide apparatuses including at least one cap for engaging at least one container, where one container contains a household fluid, having a dip tube, a handheld fluid metering device or a wand including a microprocessing unit having wireless communication hardware and software, a pump, optionally a flow meter, optionally a flow controller, a power supply, at one fluid inlet, a fluid outlet, at least one fluid conduit, and a control unit, where the processing unit, the pump, the optional flow meter, the optional flow controller, the control unit, and the power supply are in electrical communication and where the pump and the flow meter are under the control of the processing unit. In certain embodiments, the apparatuses include at least two caps having a dip tube and the wand further includes a mixing chamber for mixing at least two fluids together prior to being pumped through the pump and out the outlet. In certain embodiments, the household fluid is a laundry detergent. In other embodiments, one of the household fluids is a laundry detergent and another of the household fluids is water. In other embodiments, one of the household fluids is a laundry detergent, one of the household fluids is water and one of the household fluids is fabric softener, a stain removing fluid, a bleaching fluid, any other fluid used for washing clothes, or mixtures thereof.

Embodiments of the present disclosure broadly related to apparatuses including: (a) a laundry fluid container having a cap including a dip tube; (b) a wand including: (i) a microprocessor, (ii) a power supply, (iii) a control unit, (iv) a pump, (v) a flow meter, (vi) a fluid inlet, and (vii) a fluid outlet or dispensing head; and (c) a flexible fluid conduit interconnecting the dip tube to the fluid inlet of the wand, wherein: (1) the pump and the flow meter are under the control of the microprocessor, (2) microprocessor include wireless communication hardware and software and software for receiving output signals from the control unit and for controlling the pump and the flow controller, (3) the power supply supplies power to the microprocessor, the control unit, the pump, and the flow controller, and (4) the control unit provides a user to control the wand via the microprocessor.

Embodiments of the present disclosure broadly related to apparatuses including: (a) a plurality of laundry fluid containers, each container having a cap including a dip tube; (b) a wand including: (i) a microprocessor, (ii) a power supply, (iii) a control unit, (iv) a pump, (v) a flow meter, (vi) a plurality of flow controllers, (vii) a mixing chamber including a mixing device, (viii) an equal plurality of fluid inlets, and (ix) a fluid outlet or dispensing head; and (c) a flexible fluid conduit interconnecting the dip tube to the fluid inlet of the wand, wherein: (1) the pump, and the flow meter are under the control of the microprocessor, (2) microprocessor include wireless communication hardware and software and software for receiving output signals from the control unit and for controlling the pump and the flow controller, (3) the power supply supplies power to the microprocessor, the control unit, the pump, and the flow controller, (4) the mixing chamber and the mixer mix one or more fluid to form a mixed fluid, and (5) the control unit provides a user to control the wand via the microprocessor. In certain embodiments, the control unit includes buttons for controlling the wand. In other embodiments, the control unit includes a user feedback device such as a touchscreen for controlling the wand and for displaying information to the user.

Embodiments of the present disclosure broadly related to apparatuses including: (a) a laundry fluid container having a cap including a dip tube; (b) a wand including: (i) a microprocessor, (ii) a power supply, (iii) an control unit having a user feedback device, (iv) a pump, (v) a flow meter, (vi) a plurality of flow controllers, (vii) a mixing chamber including a mixing device, (viii) an equal plurality of fluid inlets, and (ix) a fluid outlet or dispensing head; and (c) a flexible fluid conduit interconnecting the dip tube to the fluid inlet of the wand, wherein: (1) the control unit, the pump, and the flow meter are under the control of the microprocessor, (2) microprocessor include wireless communication hardware and software and software for receiving output signals from the control unit and for controlling the pump and the flow controller, (3) the power supply supplies power to the microprocessor, the control unit, the pump, and the flow controller, (4) the mixing chamber and the mixer mix one or more fluid to form a mixed fluid, and (5) the control unit of the control unit provides a user to control the wand via the microprocessor.

Embodiments of this disclosure broadly relates to methods for including receiving a first input from a control unit of a handheld unit associated with a household fluid dispensing apparatus of this disclosure, turning on a pump of the handheld unit, and dispensing a specific amount of the fluid from a container associated with the apparatus into a household appliance. The methods may also include receiving a second input from the control unit corresponding to selecting the specific amount from a set of specific amounts. The methods may also include tracking the amount of fluid being dispensed from the container and outputting a signal corresponding to an amount of fluid remaining the container from which the fluid is being dispensed. The methods also include pulling information from a website associated with the fluid and/or appliance to set the specific amount of the fluid to be dispensed to the appliance. In certain embodiments, the signal comprises illuminating a green, yellow or red light, wherein the green light represents a fluid amount greater or equal to ¼ full, the yellow light represents a fluid amount less than ¼ full and greater or equal to ⅛ full, and the red light represents a fluid amount less than ⅛ full. In certain embodiments, the methods also include dispensing specific amounts of a plurality of fluids from a plurality of containers. In embodiments, the methods also include controlling the amount of each fluid being dispensed and tracking the amount of each fluid being dispensed. In certain embodiments, the methods also include mixing the fluids together in a mixing chamber associated with the handheld unit.

Embodiments of this disclosure provide apparatuses including at least one cap for engaging at least one container, where one container contains a household fluid, having a dip tube, a handheld fluid metering device or a wand including a microprocessing unit having wireless communication hardware and software, a pump, optionally a flow meter, optionally a flow controller, a power supply, at one fluid inlet, a fluid outlet, at least one fluid conduit, and a control unit, where the processing unit, the pump, the optional flow meter, the optional flow controller, the control unit, and the power supply are in electrical communication and where the pump and the flow meter are under the control of the processing unit. In certain embodiments, the apparatuses include at least two caps having a dip tube and the wand further includes a mixing chamber for mixing at least two fluids together prior to being pumped through the pump and out the outlet. In certain embodiments, the household fluid is a laundry detergent. In other embodiments, one of the household fluids is a laundry detergent and another of the household fluids is water. In other embodiments, one of the household fluids is a laundry detergent, one of the household fluids is water and one of the household fluids is fabric softener, a stain removing fluid, a bleaching fluid, any other fluid used for washing clothes, or mixtures thereof.

Embodiments of the present disclosure broadly related to apparatuses including: (a) a removable laundry fluid container; (b) a Base housing including: (i) a microprocessor, (ii) a power supply, (iii) a control unit having a user feedback device, (iv) a pump, (v) a flow meter, (vi) a plurality of flow controllers, (vii) a mixing chamber including a mixing device, (viii) an equal plurality of fluid inlets, and (ix) a fluid outlet or dispensing head; (c) a wand with no-drip tip, load size selection buttons and dispensing initiator button, (d) a flexible fluid conduit interconnecting the base housing to the fluid inlet of the wand, wherein: (1) the control unit, the pump, and the flow meter are under the control of the microprocessor, (2) microprocessor include wireless communication hardware and software and software for receiving output signals from the control unit and for controlling the pump and the flow controller, (3) the power supply supplies power to the microprocessor, the control unit, the pump, and the flow controller, (4) the mixing chamber and the mixer mix one or more fluid to form a mixed fluid, and (5) the control unit of the control unit provides a user to control the wand via the microprocessor.

Embodiments of the present disclosure broadly related to apparatuses including: (a) a disposable laundry fluid cartridge or multiple laundry cartridges that can contain deferent products; (b) a housing including: (i) a microprocessor, (ii) a power supply, (iii) a control unit having a user feedback device, (iv) a pump, (v) a flow meter, (vi) a plurality of flow controllers, (vii) a mixing chamber including a mixing device, (viii) an equal plurality of fluid inlets, and (ix) a fluid outlet or dispensing head; (c) a wand with no-drip tip, load size selection buttons and dispensing initiator button, (d) a flexible fluid conduit interconnecting the base housing to the fluid inlet of the wand, wherein: (1) the control unit, the pump, and the flow meter are under the control of the microprocessor, (2) microprocessor include wireless communication hardware and software and software for receiving output signals from the control unit and for controlling the pump and the flow controller, (3) the power supply supplies power to the microprocessor, the control unit, the pump, and the flow controller, (4) the mixing chamber and the mixer mix one or more fluid to form a mixed fluid, and (5) the control unit of the control unit provides a user to control the wand via the microprocessor.

Embodiments of the present disclosure broadly related to apparatuses including: (a) a reusable electronic Pipette controller including: (i) a microprocessor, (ii) a power supply, (iii) a control unit having a user feedback device, (iv) a pump, (v) a flow meter, (vi) a plurality of flow controllers, (vii) a storage chamber to store the desired amount of laundry (viii) load size selection buttons and dispensing initiator button (ix) a fluid outlet or dispensing head with no-drip tip; wherein: (1) the control unit, the pump, and the flow meter are under the control of the microprocessor, (2) microprocessor include wireless communication hardware and software and software for receiving output signals from the control unit and for controlling the pump and the flow controller, (3) the power supply supplies power to the microprocessor, the control unit, the pump, and the flow controller, (4) the mixing chamber and the mixer mix one or more fluid to form a mixed fluid, and (5) the control unit of the control unit provides a user to control the wand via the microprocessor, and (c) a container including (i) a dip tube, (ii) a cap with a one-way check valve or a fluid flow silicone check valve to create a sealed connection to the pipette.

Embodiments of the present disclosure broadly related to apparatuses including: (a) a disposable laundry fluid cartridge or multiple laundry cartridges that can contain different products; The cartridge is made in deferent shapes reflecting art objects such as animal shapes, geographical shapes such as a country map, or any other decorative shapes (b) a housing or base including: (i) a microprocessor, (ii) a power supply, (iii) a control unit having a user feedback device, (iv) a pump, (v) a flow meter, (vi) a plurality of flow controllers, (vii) a mixing chamber including a mixing device, (viii) an equal plurality of fluid inlets, and (ix) a fluid outlet or dispensing head; (c) a wand with no-drip tip, load size selection buttons and dispensing initiator button, (d) a flexible fluid conduit interconnecting the base housing to the fluid inlet of the wand, wherein: (1) the control unit, the pump, and the flow meter are under the control of the microprocessor, (2) microprocessor include wireless communication hardware and software and software for receiving output signals from the control unit and for controlling the pump and the flow controller, (3) the power supply supplies power to the microprocessor, the control unit, the pump, and the flow controller, (4) the mixing chamber and the mixer mix one or more fluid to form a mixed fluid, and (5) the control unit of the control unit provides a user to control the wand via the microprocessor.

Embodiments of the present disclosure broadly related to apparatuses including: (a) a disposable laundry fluid cartridge or multiple laundry cartridges that can contain different products; The cartridge is made in deferent shapes reflecting art objects such as animal shapes, geographical shapes such as a country map, or any other decorative shapes (b) a housing or base including: (i) a microprocessor, (ii) a power supply, (iii) a control unit having a user feedback device, (iv) a pump, (v) a flow meter, (vi) a plurality of flow controllers, (vii) a mixing chamber including a mixing device, (viii) an equal plurality of fluid inlets, and (ix) a fluid outlet or dispensing head; (c) a wand with no-drip tip, load size selection buttons and dispensing initiator button, (d) a flexible fluid conduit interconnecting the base housing to the fluid inlet of the wand, wherein: (1) the control unit, the pump, and the flow meter are under the control of the microprocessor, (2) microprocessor include wireless communication hardware and software and software for receiving output signals from the control unit and for controlling the pump and the flow controller, (3) the power supply supplies power to the microprocessor, the control unit, the pump, and the flow controller, (4) the mixing chamber and the mixer mix one or more fluid to form a mixed fluid, and (5) the control unit of the control unit provides a user to control the wand via the microprocessor.

Suitable Components for use in the Disclosure

Household and Industrial Fluids

Suitable ready to use household and industrial fluids include, without limitation, laundry detergents, chlorine containing bleaches, non-chlorine-containing bleaches, fabric softeners, stain removing fluids, dishwashing fluids, laundry pre-spotters, pool cleaning fluids and concentrated fluids such as bathroom cleaners, tub cleaners, tile cleaner, toilet bowl cleaner, general cleaner and disinfectant, window and glass cleaner, or mixtures and combinations thereof.

Micro Pumps

Suitable micro pumps for use in this disclosure include, without limitation, peristaltic, piezoelectric micro pumps, metering pumps, any other micro pump, or mixtures and combinations thereof.

Micro Flow Meters

Suitable micro flow meters for use in this disclosure include, without limitation, metal or plastic microflow meters such as microflow meters available from MOJO Technology Co., Limited, Bitspower flow sensor available from Watercooling, UK, microflow meters available from B.I.O-TECH e.K., microflow meters available from OMEGA Engineering is a subsidiary of Spectris PLC, microflow meters available from Siemens, and any other manufacturer of micro flow meters.

Micro Flow Controllers

Suitable micro flow controller for use in this disclosure include, without limitation, metal or plastic micro flow controller such as micro flow controller available from MOJO Technology Co., Limited, micro flow controller available from Watercooling, UK, micro flow controller available from B.I.O-TECH e.K., micro flow controller available from OMEGA Engineering is a subsidiary of Spectris PLC, micro flow controller available from Siemens, and any other manufacturer of micro flow meters.

Micro Processing Units

Suitable micro processing units or microprocessors for use in the present disclosure include, without limitation, digital microprocessing units (DPUs), analog microprocessing units (APUs), micro Field Programmable Gate Arrays (FPGAs), any other technology that can receive motion sensor output and generate command and/or control functions for objects under the control of the processing unit, or mixtures and combinations thereof.

Processing Units and MicroProcessing Units

Suitable digital processing units, digital processors, (DPUs) micro processing units, and digital microprocessors (DmPUs) include, without limitation, any digital processing unit capable of accepting input from a plurality of devices and converting at least some of the input into output designed to select and/or control attributes of one or more of the devices. Exemplary examples of such DPUs include, without limitation, microprocessor, microcontrollers, or the like manufactured by Intel, Motorola, Ericsson, HP, Samsung, Hitachi, NRC, Applied Materials, AMD, Cyrix, Sun Microsystem, Philips, National Semiconductor, Qualcomm, ARM, TDK, Invensense, Xilinx, Altera or any other manufacture of microprocessors or microcontrollers.

Suitable analog processing units or processors (APUs) and micro processing units or analog microprocessors (AmPUs) include, without limitation, any analog processing unit capable of accepting input from a plurality of devices and converting at least some of the input into output designed to control attributes of one or more of the devices. Such analog devices are available from manufacturers such as Analog Devices Inc.

User Feedback Units

Suitable user feedback units include, without limitation, a haptic (touch) device, an audio device, a visual device, and/or an audiovisual device. Exemplary examples of audio devices include, without limitation, speakers or any other device the generate audio frequency vibrations. Exemplary examples of visual devices include, without limitation, liquid crystal displays, light emitting diode displays, organic light emitting diode displays, plasma displays, touch screens, touch sensitive input/output devices, holographic display devices, optical input/output device, and any other optical input/output device that permits a user to receive user intended inputs and outputs. Exemplary examples of audiovisual devices include, without limitation, liquid crystal displays including an audio component, light emitting diode displays including an audio component, organic light emitting diode displays including an audio component, plasma displays including an audio component, touch screens including an audio component, touch sensitive input/output devices including an audio component, holographic display devices including an audio component, optical input/output devices including an audio component, and any other optical input/output device that permits a user to receive user intended inputs and outputs including an audio component.

Household and Industrial Appliances

Suitable household and industrial appliance include, without limitation, washing machines, dish washing machines, and drawer dish washing machines.

DETAILED DESCRIPTION OF THE DRAWINGS OF THE DISCLOSURE

General Apparatus—First Type

Figure 1:
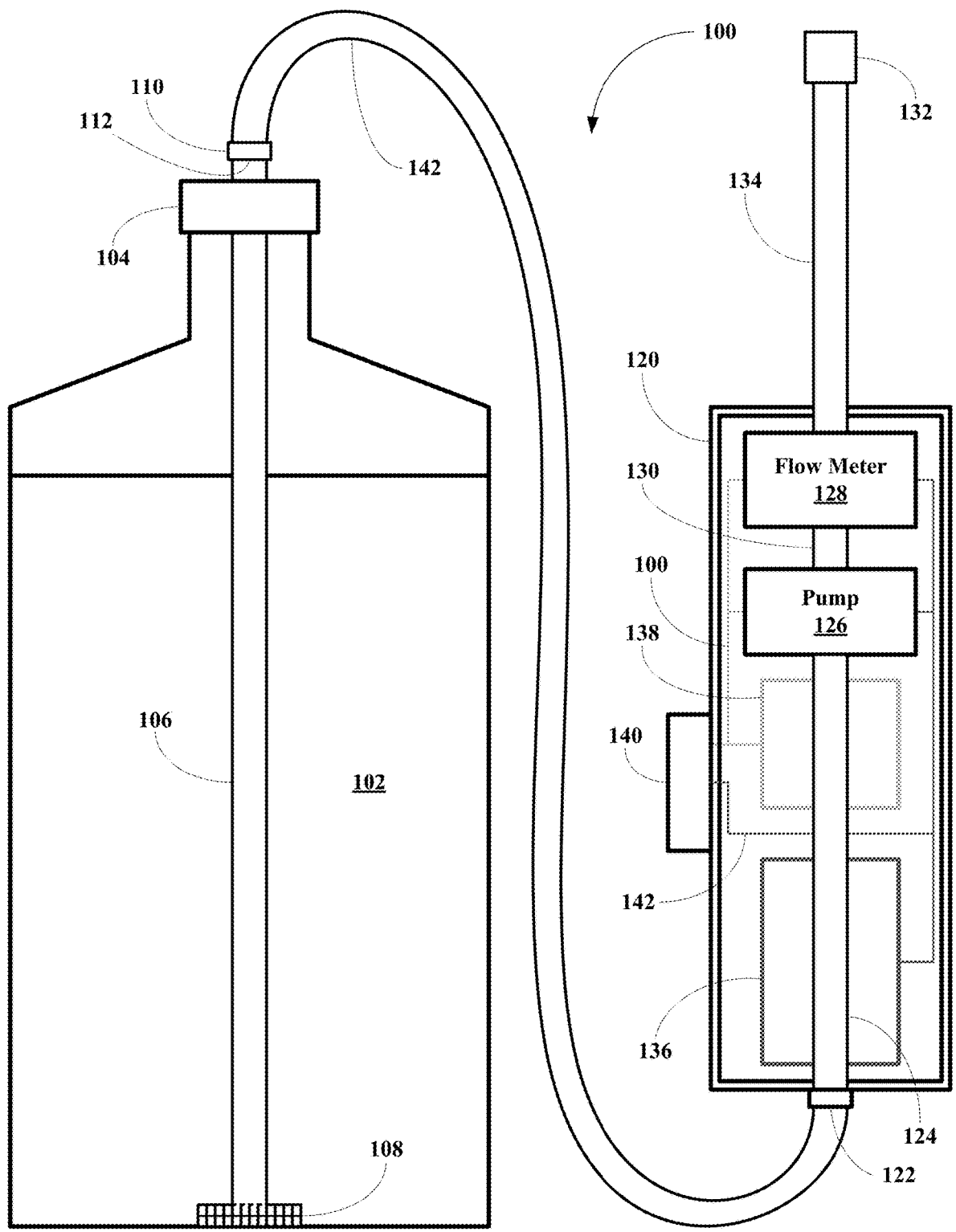
FIG. 1 depicts an embodiment of a dispensing apparatus of this disclosure, where the wand includes a pump, a flow meter, a microprocessor, and a power supply.

Referring now to FIG. 1, an embodiment of dispensing apparatus of this disclosure, generally 100, is shown to include a fluid container 102 including a cap 104 having a dip tube 106 including a wire mesh fluid inlet 108, and an outlet connector 110 associated with a fluid outlet 112.

The apparatus 100 also includes a handheld fluid dispensing device or wand 120 including an fluid inlet connector 122, a first fluid conduit 124, and a pump 126. The first fluid conduit 124 interconnects the inlet connector 122 and the pump 126. The wand 120 also includes a flow meter 128, a second fluid conduit 130, a fluid wand outlet head 132, and a third fluid conduit 134, where the second fluid conduit 130 interconnects the pump 126 to the flow meter 128 and where the third conduit 134 interconnects the flow meter 128 and the outlet head 132. The wand 120 also includes a power supply 136, a microprocessing unit 138, and a control unit 140. The power supply 136 supplies power to the pump 126, the flow meter 128, and the control unit 140 via electrical wires 142. The microprocessor 138 is in two-way communication with the pump 126, the flow meter 128, and the control unit 140 and is configured to receive an output signal or signals from the control unit 140, to turn the pump 126 ON or OFF, to monitor the fluid flowing through the flow meter 128 and to turn the pump 126 OFF when the flow meter output indicates that a pre-defined or pre-set amount of fluid has passed through the flow meter 128. Of course, it should be recognized that the pump 126 and flow meter 128 maybe integrated into a single metering pump. Additionally, the microprocessor 138 is also configured to keep track of the amount of fluid dispensed and to notify a user when the fluid in the container containing the fluid is low and needs to be replaced and/or refilled.

The apparatus 100 also includes a flexible fluid conduit 144 interconnecting the fluid outlet connector 110 to the fluid inlet connector 122. The flexible fluid conduit 144 may be of any length, but should be of sufficient length so that the outlet head 132 of the wand 120 may be inserted into a fluid inlet associated with an appliance, a pool, a vehicle, or any other structure that need a fluid to operate.

Handheld Dispensing Device or Wand

Pump and Flow Meter

Referring now to FIG. 2A, another embodiment of a wand of this disclosure, generally 200, is shown to include a first fluid inlet connector 202, a second fluid inlet connector 204, a two legged fluid conduit 206, and a pump 208. The two-legged fluid conduit 206 interconnects the inlet connectors 202 and 204 and the pump 208 and supplies two different fluid to the pump 208. It should be recognized that the two legs of the two-legged conduit 206 may be of different sizes to control the relative ratio of the two fluid entering the pump 208.

The wand 200 also includes a flow meter 210, a second fluid conduit 212, a fluid wand outlet head 214, and a third fluid conduit 216, where the second fluid conduit 212 interconnects the pump 208 and the flow meter 210 and where the third conduit 216 interconnects the flow meter 210 and the outlet head 214.

The wand 200 also includes a power supply 218, a microprocessing unit 220, and a control unit 222.

The power supply 218 supplies power to the pump 208, the flow meter 210, and the control unit 222 via electrical wires 224. The microprocessor 220 is in two-way communication with the pump 208, the flow meter 210, and the control unit 222 via communication pathways 226.

The microprocessor 220 is configured to receive an output signal or signals from the control unit 222, to turn the pump 208 ON or OFF, to monitor the fluid flowing through the flow meter 210 and to turn the pump 208 OFF when the flow meter output indicates that a pre-defined or pre-set amount of fluid has passed through the flow meter 210.

Additionally, the microprocessor 220 is also configured to keep track of the amount of fluid dispensed and to notify a user when the fluid in the container containing the fluid is low and needs to be replaced and/or refilled. Of course, it should be recognized that the pump 208 and flow meter 210 may be integrated into a single metering pump.

Mixing Chamber, Pump, and Flow Meter

Referring now to FIG. 2B, another embodiment of a wand of this disclosure, generally 250, is shown to include a first fluid inlet connector 252, a second fluid inlet connector 254, a first fluid conduit 256, second fluid conduit 258, and a mixing chamber 260. The first and second fluid conduits 256 and 258 interconnect the inlet connectors 252 and 254 and the mixing chamber 260. It should be recognized that the two conduits 256 and 258 may be of different sizes to control the relative ratio of the two fluids entering the mixing chamber 260.

The wand 250 also includes a pump 262, a third fluid conduit 264, a flow meter 266, a fourth fluid conduit 268, and a fluid wand outlet head 270, where the third fluid conduit 264 interconnects the pump 262 to the flow meter 266 and where the fourth conduit 268 interconnects the flow meter 266 and the outlet head 270.

The wand 250 also includes a power supply 272, a microprocessing unit 274, and a control unit 276. The power supply 272 supplies power to the mixing chamber 260 with the mixing chamber includes a mixer (not shown), the pump 262, the flow meter 266, and the control unit 276 via electrical wires 278.

The microprocessor 274 is in two-way communication with the pump 262, the flow meter 266, and the control unit 276 via communication pathways 280. The microprocessor 274 is configured to receive an output signal or signals from the control unit 276, to turn the pump 262 ON or OFF, to monitor the fluid flowing through the flow meter 266 and to turn the pump 262 OFF when the flow meter output indicates that a pre-defined or pre-set amount of fluid has passed through the flow meter 266.

Additionally, the microprocessor 274 is also configured to keep track of the amount of fluid dispensed and to notify a user when the fluid in the container containing the fluid is low and needs to be replaced and/or refilled. Of course, it should be recognized that the pump 262 and flow meter 266 may be integrated into a single metering pump.

Flow Controllers, Pump, and Flow Meter

Figure 3A:
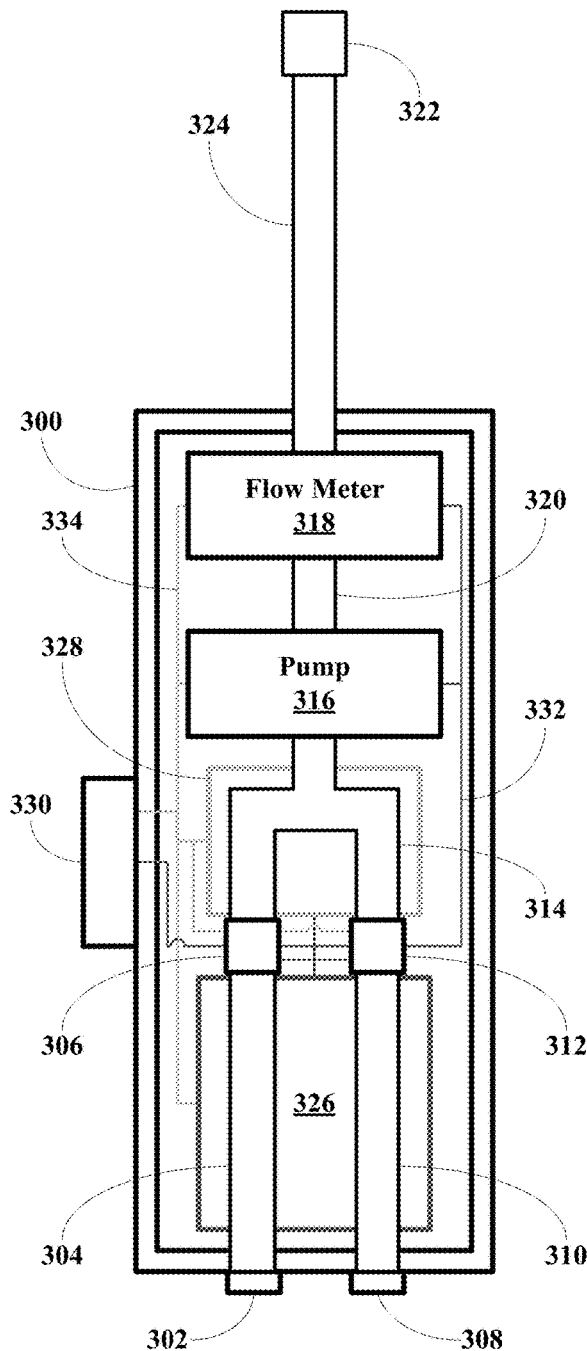
FIG. 3A depicts another embodiment of a wand of this disclosure, where the wand includes flow controllers, a pump, a flow meter, a microprocessor, and a power supply and capable of dispensing two fluids.

Referring now to FIG. 3A, another embodiment of a wand of this disclosure, generally 300, is shown to include a first fluid inlet connector 302, a first fluid conduit 304, a first flow controller 306, a second fluid inlet connector 308, a second fluid conduit 310, a second flow controller 312, a two-legged fluid conduit 314, and a pump 316. The first conduit 304 interconnects the first inlet connector 302 and the first flow controller 306. The second conduit 310 interconnects the second inlet connector 308 and the second flow controller 312. The two legged fluid conduit 314 interconnects the flow control controllers 306 and 312 and the pump 316 and supplies two different fluid to the pump 316 at a controlled rate.

The wand 300 also includes a flow meter 318, a third fluid conduit 320, a fluid wand outlet head 322, and a fourth fluid conduit 324, where the third fluid conduit 320 interconnects the pump 316 and the flow meter 318 and where the fourth conduit 324 interconnects the flow meter 318 and the outlet head 322.

The wand 300 also includes a power supply 326, a microprocessing unit 328, and a control unit 330.

The power supply 326 supplies power to the flow controllers 306 and 312, pump 316, the flow meter 318, and the control unit 330 via electrical wires 332.

The microprocessor 328 is in two-way communication with the flow controllers 306 and 312, pump 316, the flow meter 318, and the control unit 332 via communication pathways 334. The microprocessor 326 is configured to receive an output signal or signals from the control unit 330, to turn the pump 316 ON or OFF, to monitor the fluid flowing through the flow meter 318 and to turn the pump 316 OFF when the flow meter output indicates that a pre-defined or pre-set amount of fluid has passed through the flow meter 318.

Additionally, the microprocessor 328 is also configured to keep track of the amount of fluid dispensed and to notify a user when the fluid in the container containing the fluid is low and needs to be replaced and/or refilled. Of course, it should be recognized that the pump 316 and flow meter 318 may be integrated into a single metering pump.

Flow Controllers, Mixing Chamber, Pump, and Flow Meter

Figure 3B:
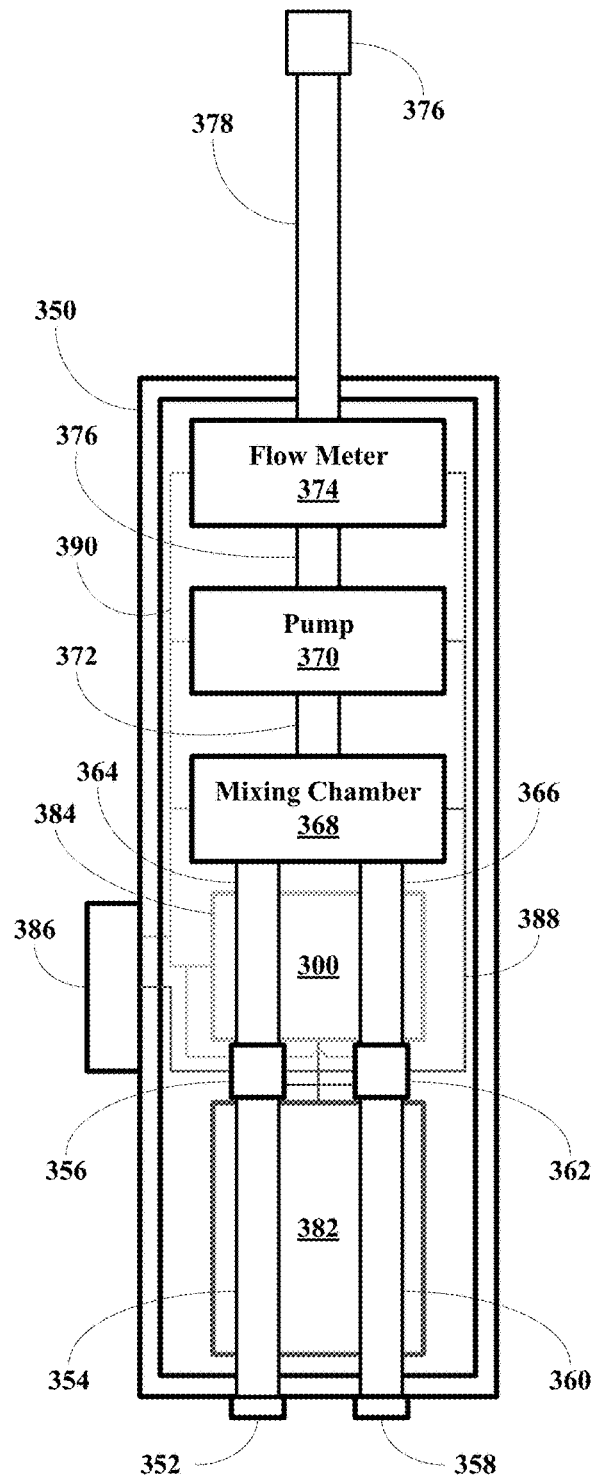
FIG. 3B depicts another embodiment of a wand of this disclosure, where the wand includes flow controllers, a mixing chamber, a pump, a flow meter, a microprocessor, and a power supply and capable of dispensing two fluids.

Referring now to FIG. 3B, another embodiment of a wand of this disclosure, generally 350, is shown to include a first fluid inlet connector 352, a first fluid conduit 354, a first flow controller 356, a second fluid inlet connector 358, a second fluid conduit 360, a second flow controller 362, a third fluid conduit 364, and a fourth fluid conduit 366, and a mixing chamber 368. The first conduit 354 interconnects the first inlet connector 352 and the first flow controller 356. The second conduit 360 interconnects the second inlet connector 358 and the second flow controller 362. The third and fourth conduits 364 and 366 interconnect the flow controllers 356 and 362 and the mixing chamber 368 and supplies two different fluids to the mixing chamber 368 at a controlled rate.

The wand 350 also includes a pump 370, a fifth fluid conduit 372, a flow meter 374, a sixth fluid conduit 376, a fluid wand outlet head 378, and a seventh fluid conduit 380, where the fifth fluid conduit 372 interconnects the pump 370 to the mixing chamber 368, the sixth fluid conduit 376 interconnects the pump 370 and the flow meter 374 and where the seventh fluid conduit 380 interconnects the flow meter 374 and the outlet head 378.

The wand 350 also includes a power supply 382, a microprocessing unit 384, and a control unit 386.

The power supply 382 supplies power to the pump 370, the flow meter 374, and the control unit 386 via electrical wires 388.

The microprocessor 384 is in two-way communication with the flow controllers 356 and 362, the pump 370, the flow meter 374, and the control unit 386 via communication pathways 390. The microprocessor 384 is configured to receive an output signal or signals from the control unit 386, to adjust the flow controllers 356 and 362, to turn the pump 370 ON or OFF, to monitor the fluid flowing through the flow meter 374 and to turn the pump 370 OFF when the flow meter output indicates that a pre-defined or pre-set amount of fluid has passed through the flow meter 374.

Additionally, the microprocessor 370 is also configured to keep track of the amount of fluid dispensed and to notify a user when the fluid in the container containing the fluid is low and needs to be replaced and/or refilled. Of course, it should be recognized that the pump 370 and flow meter 374 may be integrated into a single metering pump.

Containers

Referring now to FIG. 4A, another embodiment of a container of this disclosure, generally 400, is shown to include an outer shell 402, a neck 404, a cap 406 having a hose connector 408, and a dip tube 410 having a fretted intake distal end 412 and a proximal end 414 terminating in the connector 408. The container 400 further includes a sump region 416 in which the distal end 414 is situated. The sump region 416 is formed by a ramp 418, which improves drainage of a fluid contained in the container 400.

Referring now to FIG. 4B, another embodiment of a container of this disclosure, generally 450, is shown to include an outer shell 452, a neck 454, a cap 456 having a hose connector 458, and a dip tube 460 having a fretted intake distal end 462 and a proximal end 464 terminating in the connector 458. The container 450 further includes a sump region 466 in which the distal end 462 is situated. The sump region 466 is formed by a step 468, which improves drainage of a fluid contained in the container 450.

Specific Apparatuses

Figure 5A:
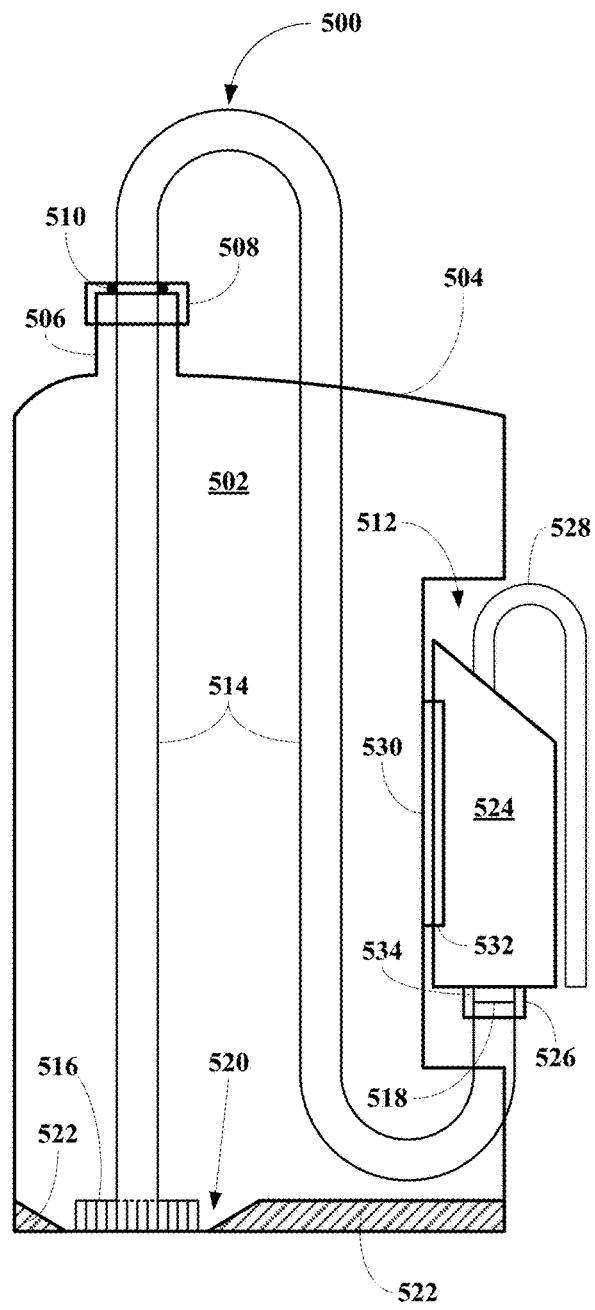
FIG. 5A depicts another embodiment of an apparatus of this disclosure including another designed container and a wand.

Referring now to FIG. 5A, another embodiment of an apparatus of this disclosure, generally 500, is shown to include a container 502 comprising an outer shell 504, a neck 506, a cap 508 having an O-ring 510, a wand receiving slot 512, and a fluid conduit 514 having a fretted intake distal end 516 and a proximate end 518. The container 502 further includes a sump region 520 in which the distal end 516 is situated. The sump region 520 is formed by a ramp 522, which improves drainage of a fluid contained in the container 502. The apparatus 500 also includes a wand 524 having a connector 526 and a dispensing conduit 528. The apparatus 500 include a protrusion 530, while the wand 524 includes a slot 532, where the slot 532 in the wand 524 is designed to receive the protrusion 530 so that the wand 524 may be detachably affixed to the container 502. The wand connector 526 is designed to receive the proximal end 518 of the fluid conduit 514 and to connect it to an internal wand fluid conduit 534.

Figure 5B:
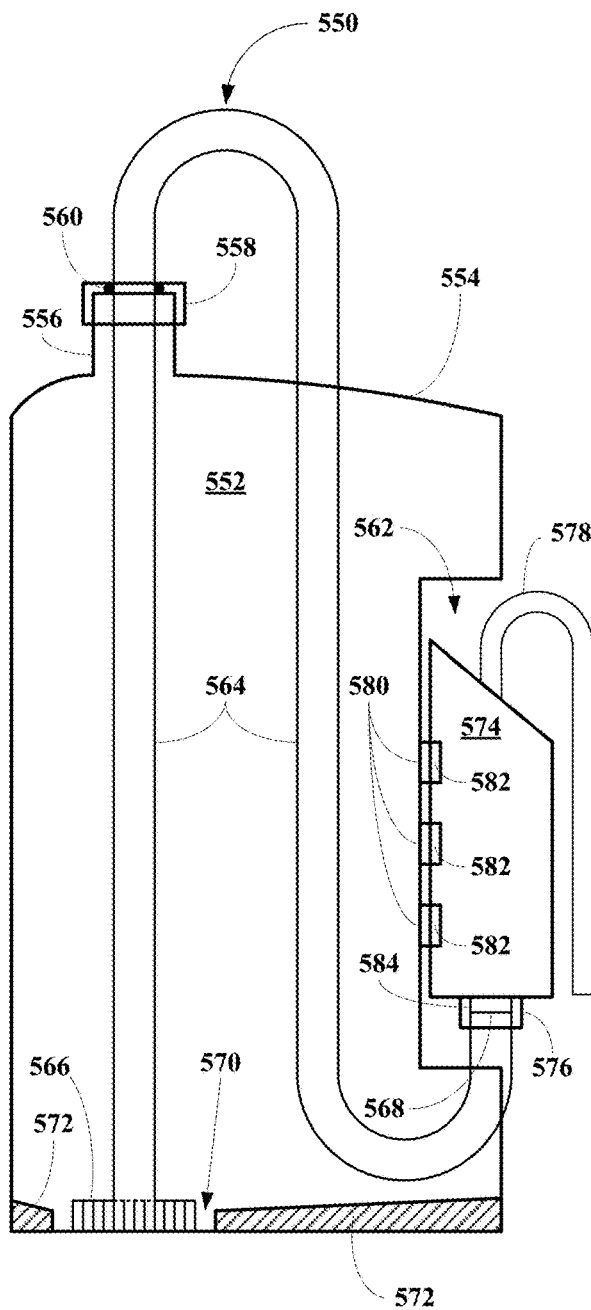
FIG. 5B depicts another embodiment of an apparatus of this disclosure including another designed container and a wand.

Referring now to FIG. 5B, another embodiment of an apparatus of this disclosure, generally 550, is shown to include container 552 comprising an outer shell 554, a neck 556, a cap 558 having an O-ring 560, a wand receiving slot 562, and a fluid conduit 564 having a fretted intake distal end 566 and a proximate end 568. The container 552 further includes a sump region 570 in which the distal end 566 is situated. The sump region 570 is formed by a ramp 572, which improve drainage of a fluid contained in the container 552. The apparatus 550 also includes a wand 574 having a connector 576 and a dispensing conduit 578. The container also includes three container magnets 580, while the wand 574 includes three wand magnets 582, where the container magnets 580 and the wand magnets 582 are designed to engage each other so that the wand 574 may be detachably affixed to the container 552; of course, the container magnets 580 are oppositely polled relative to the wand magnets 582. The wand connector 576 is designed to receive the proximal end 568 of the fluid conduit 564 and to connect it to an internal wand fluid conduit 584.

Dip Tubes

Figures 6A, 6B, 6C, 6D:
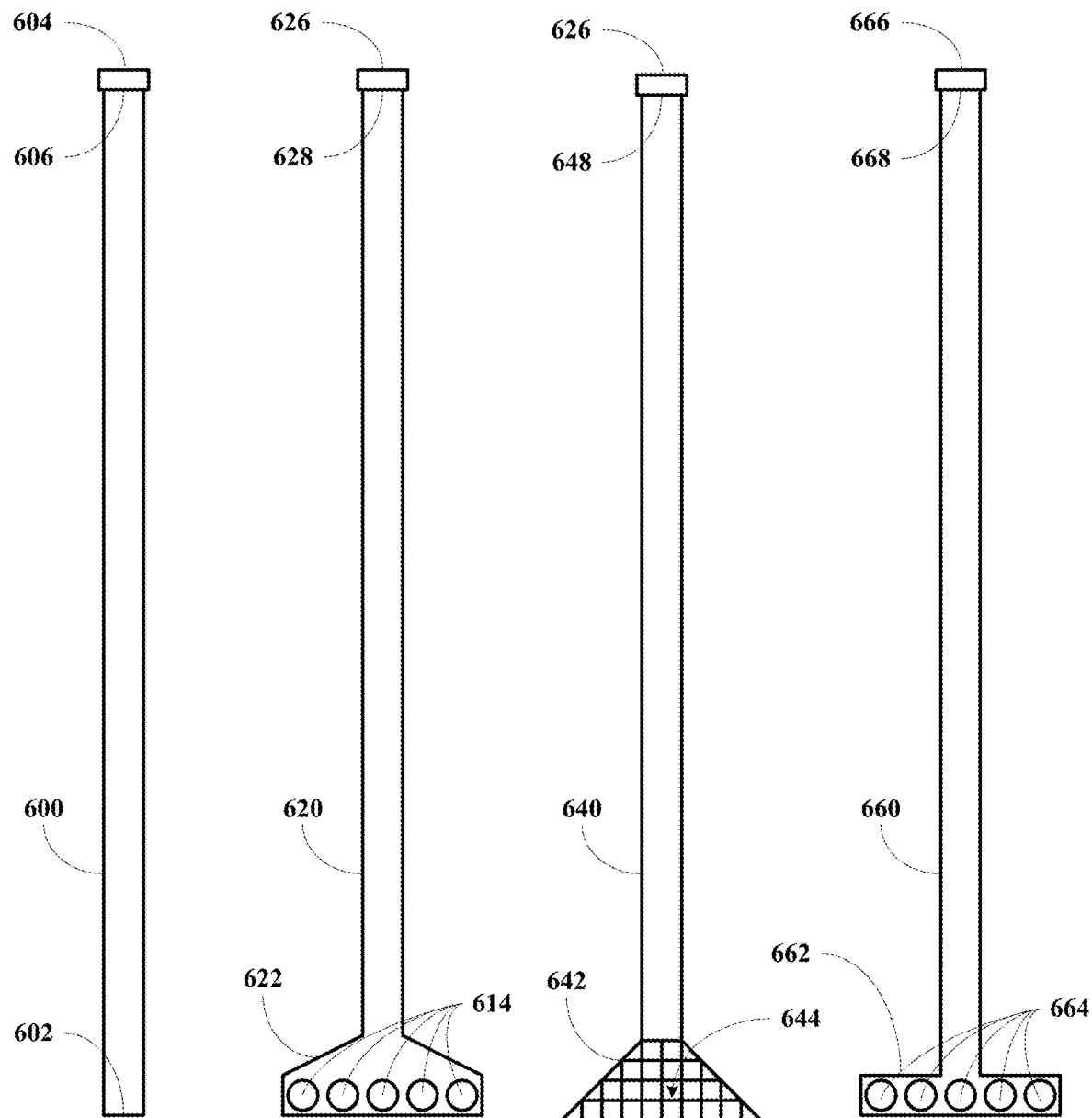
FIG. 6A depicts another embodiment of a dip tube of this disclosure including a simple inlet.
FIG. 6B depicts another embodiment of a dip tube of this disclosure including a flared inlet with circular apertures.
FIG. 6C depicts another embodiment of a dip tube of this disclosure including a triangular wire mesh flared inlet.
FIG. 6D depicts another embodiment of a dip tube of this disclosure including a rectangular flared inlet with circular apertures.

Referring now to FIG. 6A, another embodiment of a dip tube 600 include a straight inlet 602 and a connector 604 associated with an outlet 606, where fluid is sucked from the inlet 602 through the dip tube 600.

Referring now to FIG. 6B, another embodiment of a dip tube 620 include a flared inlet 622 having circular apertures 624 and a connector 626 associated with an outlet 628.

Referring now to FIG. 6C, another embodiment of a dip tube 640 include a triangular inlet 642 having wire mesh 644 and a connector 646 associated with an outlet 648.

Referring now to FIG. 6D, another embodiment of a dip tube 660 include a rectangular flared inlet 662 having circular apertures 664 and a connector 666 associated with an outlet 668.

Control Unit

Referring now to FIG. 7A, an embodiment of a control unit 700 is shown to include an ON/OFF button 702, a first amount selection button 704, a second amount selection button 706 and a speaker 708. Alternatively, the buttons 702, 704, and 706 may be replaced by a dial selector. The buttons 702, 704, and 706 produce output signals that are forwarded to the processing unit, which controls the other wand components to dispense an amount of fluid from the fluid container. The processing unit may send signals to the speaker 708 that may also notify the user concerning fluid remaining in the container or when an amount of fluid has been dispenses.

Referring now to FIG. 7B, another embodiment of a control unit 510 is shown to include an ON/OFF button 512, a first amount selection button 514, a variable amount slider controller 516, a speaker 518, and indicator LEDs 520. The buttons 712 and 714, and the slider controller 716 produce output signals that are forwarded to the processing unit, which controls the other wand components to dispense an amount of fluid from the fluid container. The LEDs 720 receive output from the processing unit to indicate the amount of fluid remaining in the fluid container. In certain embodiments, the right LED is a green LED and indicates that the fluid in the fluid container is between fluid and ¼ full. The middle LED is a yellow LED indicates that the fluid is the container is below ¼ full and ⅛ full. The left LED is a red LED indicates that the fluid is less than ⅛ full. These colors are used to notify the user as to the fluid level in the container. The processing unit may send signals to the speaker 718 that may also notify the user concerning fluid remaining in the container or when an amount of fluid has been dispenses.

Referring now to FIG. 7C, another embodiment of a control unit 730 is shown to include an ON/OFF button 732, a display 734, a speaker 736, and indicator LEDs 738. The buttons 732 and the display 734 produce output signals that are forwarded to the processing unit, which controls the other wand components to dispense an amount of fluid from the fluid container. The display 734 also receives output signals from the processing unit and displays information to the user as to amount of fluid dispensed and other information. The LEDs 738 receive output from the processing unit to indicate the amount of fluid remaining in the fluid container. In certain embodiments, the right LED is a green LED and indicates that the fluid in the fluid container is between fluid and ¼ full. The middle LED is a yellow LED indicates that the fluid is the container is below ¼ full and ⅛ full. The left LED is a red LED indicates that the fluid is less than ⅛ full. These colors are used to notify the user as to the fluid level in the container. The processing unit may send signals to the speaker 736 that may also notify the user concerning fluid remaining in the container or when an amount of fluid has been dispenses.

Referring now to FIG. 7D, another embodiment of a control unit 750 is shown to include a display 752 and a speaker 754. The processing unit may send signals to the speaker 754 that may also notify the user concerning fluid remaining in the container or when an amount of fluid has been dispenses. The display 752 sends signals to the processing unit and receives signals from the processing unit concerning the dispensing of fluids and notifying the user about fluid levels and amount or amount of fluid or fluids dispensed.

Referring now to FIG. 7E, another embodiment of a control unit 760 is shown to include a display 762, a speaker 764, and LEDs 766. The processing unit may send signals to the speaker 764 that may also notify the user concerning fluid remaining in the container or when an amount of fluid has been dispenses. The display 762 sends signals to the processing unit and receives signals from the processing unit concerning the dispensing of fluids and notifying the user about fluid levels and amount or amount of fluid or fluids dispensed. The LEDs 766 receive output from the processing unit to indicate the amount of fluid remaining in the fluid container. In certain embodiments, the right LED is a green LED and indicates that the fluid in the fluid container is between fluid and ¼ full. The middle LED is a yellow LED indicates that the fluid is the container is below ¼ full and ⅛ full. The left LED is a red LED indicates that the fluid is less than ⅛ full. These colors are used to notify the user as to the fluid level in the container.

Referring now to FIG. 7F, another embodiment of a control unit 780 is shown to include a display 782. The display 782 sends signals to the processing unit and receives signals from the processing unit concerning the dispensing of fluids and notifying the user about fluid levels and amount or amount of fluid or fluids dispensed.

General Apparatus—Second Type

Apparatus with a Single Reservoir

Figure 8:
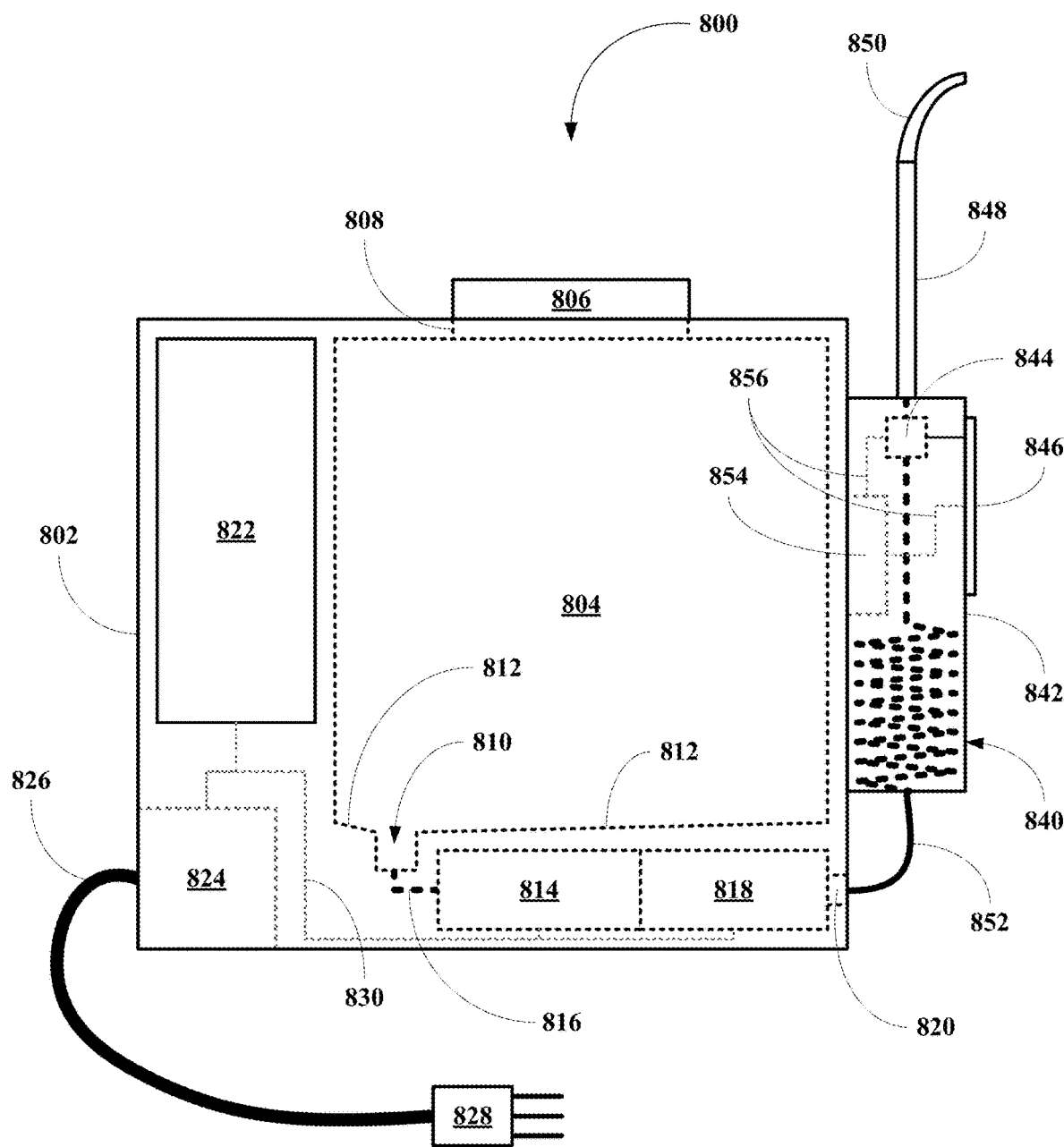
FIG. 8 depicts another embodiment of a fluid dispensing apparatus of this disclosure, where the apparatus includes a fluid reservoir, a wand, a pump, a flow meter, a microprocessor, and a power supply.

Referring now to FIG. 8, another embodiment of dispensing apparatus of this disclosure, generally 800, is shown to include a housing 802 containing a fluid reservoir 804 including a cap 806, a neck 808, a fluid outlet 810, and drainage ramps 812. The apparatus 800 also includes a flow controller 814 connected to the fluid outlet 810 via a fluid conduit 816. The flow controller 814 is in fluid communication with a pump 818 having an outlet 820. The apparatus 800 also includes a control panel 822 and a power supply 824 having a power cord 826 having a plug 828. The power supply 824 is connected to the panel 822, the flow controller 814 and the pump 818 via wires 830. The control panel 822 includes a microprocessor (not shown) and may be of any of the configuration depicted in FIGS. 7A-F.

The apparatus 800 also includes a handheld fluid dispensing device or wand 840 including a wand housing 842 containing a control valve 844, a wand control panel 846, and a dispensing conduit 848 having a nozzle 850. The control valve 844 is connected to the outlet 820 of the pump 818 via a flexible fluid conduit 852. The wand 840 also includes a power supply 854. The power supply 854 is connected to the wand panel 846 and the control valve 844 via wires 856. The wand control panel 846 includes a microprocessor (not shown) and may be of any of the configuration depicted in FIGS. 7A-F.

Apparatus with Two Reservoirs

Figure 9:
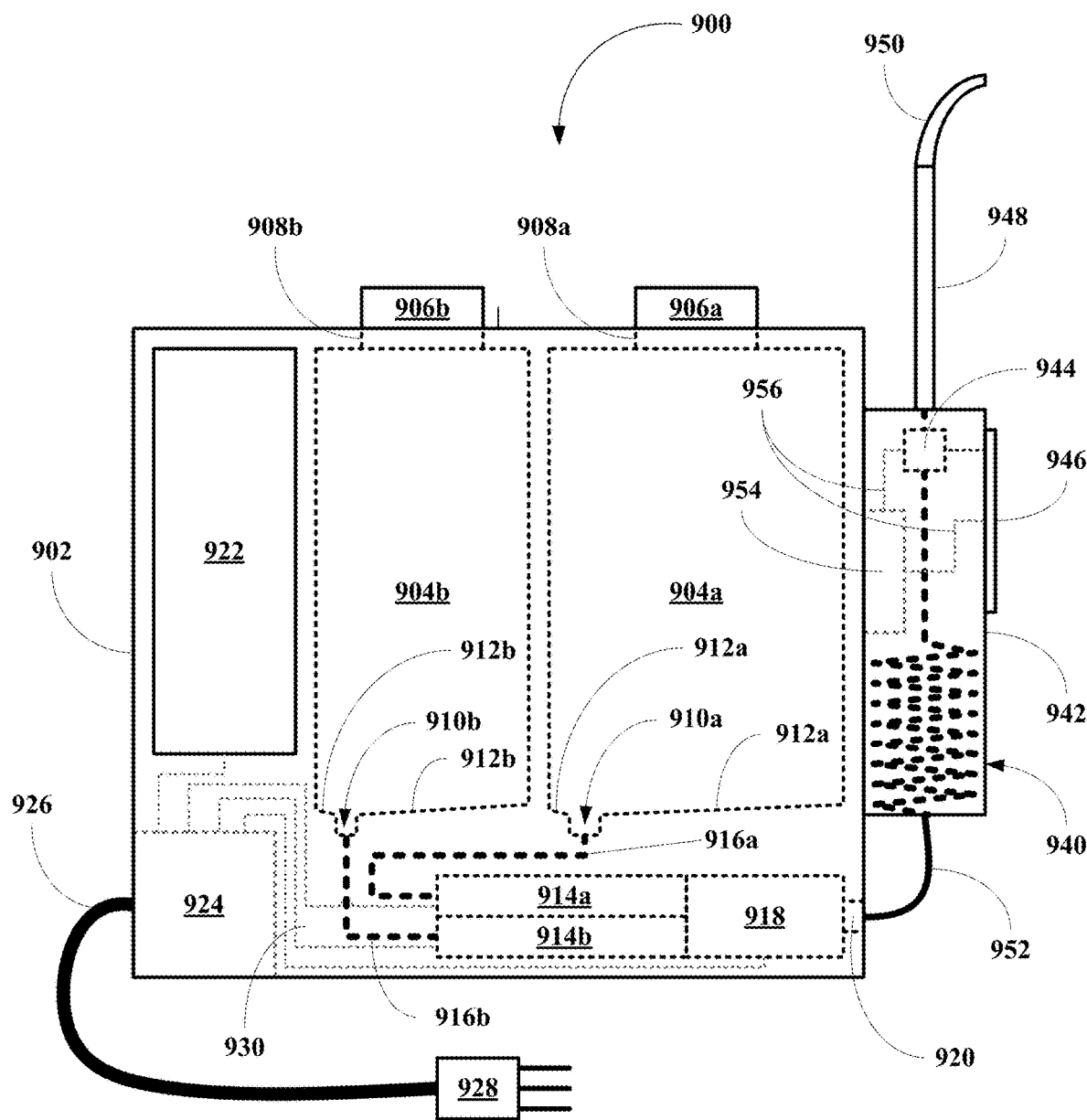
FIG. 9 depicts another embodiment of a fluid dispensing apparatus of this disclosure, where the apparatus includes two fluid reservoirs, a wand, a pump, flow meters, a microprocessor, and a power supply.

Referring now to FIG. 9, another embodiment of dispensing apparatus of this disclosure, generally 900, is shown to include a housing 902 containing two fluid reservoirs 904a&b including caps 906a&b, necks 908a&b, fluid outlets 910a&b, and drainage ramps 912a&b. The apparatus 900 also includes two flow controllers 914 connected to the fluid outlets 910a&b via fluid conduit 916a&b. The flow controllers 914a&b are in fluid communication with a pump 918 having an outlet 920. The apparatus 900 also includes a control panel 922 and a power supply 924 having a power cord 926 having a plug 928. The power supply 924 is connected to the panel 922, the flow controllers 914a&b and the pump 918 via wires 930. The control panel 922 includes a microprocessor (not shown) and may be of any of the configuration depicted in FIGS. 7A-F.

The apparatus 900 also includes a handheld fluid dispensing device or wand 940 including a wand housing 942 containing a control valve 944, a wand control panel 946, and a dispensing conduit 948 having a nozzle 950. The control valve 944 is connected to the outlet 920 of the pump 918 via a flexible fluid conduit 952. The wand 940 also includes a power supply 954. The power supply 954 is connected to the wand panel 946 and the control valve 944 via wires 956. The wand control panel 946 includes a microprocessor (not shown) and may be of any of the configuration depicted in FIGS. 7A-F.

Apparatus with Three Reservoirs

Figure 10:
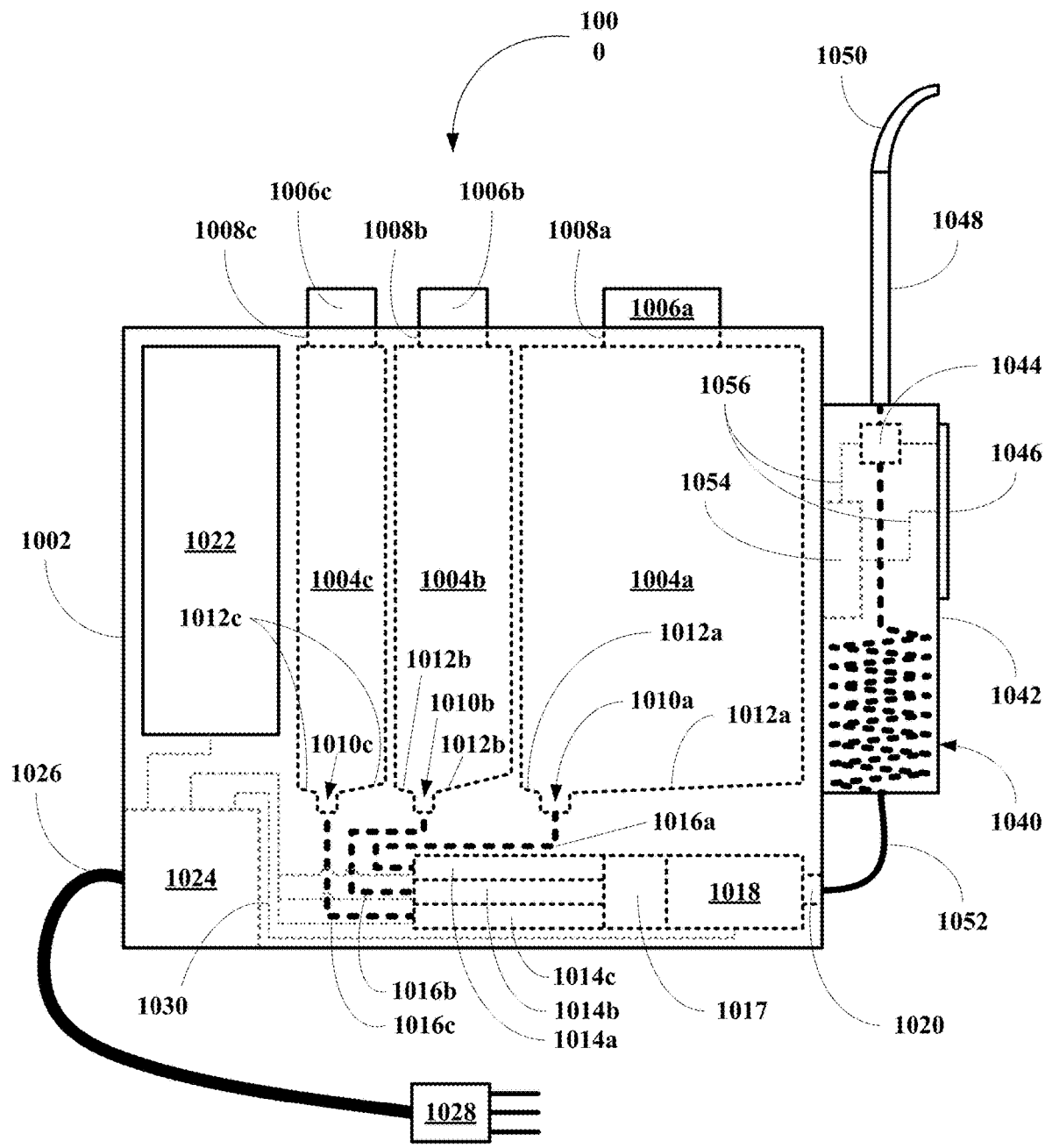
FIG. 10 depicts another embodiment of a fluid dispensing apparatus of this disclosure, where the apparatus includes three fluid reservoir, a wand, a pump, flow meters, a microprocessor, and a power supply.

Referring now to FIG. 10, another embodiment of dispensing apparatus of this disclosure, generally 1000, is shown to include a housing 1002 containing two fluid reservoirs 1004a-c including caps 1006a-c, necks 1008a-c, fluid outlets 1010a-c, and drainage ramps 1012a-c. The apparatus 1000 also includes three flow controllers 1014 connected to the fluid outlets 1010a-c via fluid conduit 1016a-c. The apparatus 1000 also includes a mixing chamber 1017 interposed between the flow controllers 1014a-c and the pump 1018. The flow controllers 1014a-c are in fluid communication with a pump 1018 having an outlet 1020. The apparatus 1000 also includes a control panel 1022 and a power supply 1024 having a power cord 1026 having a plug 1028. The power supply 1024 is connected to the panel 1022, the flow controllers 1014a-c and the pump 1018 via wires 1030. The control panel 1022 includes a microprocessor (not shown) and may be of any of the configuration depicted in FIGS. 7A-F.

The apparatus 1000 also includes a handheld fluid dispensing device or wand 1040 including a wand housing 1042 containing a control valve 1044, a wand control panel 1046, and a dispensing conduit 1048 having a nozzle 1050. The control valve 1044 is connected to the outlet 1020 of the pump 1018 via a flexible fluid conduit 1052. The wand 1040 also includes a power supply 1054. The power supply 1054 is connected to the wand panel 1046 and the control valve 1044 via wires 1056. The wand control panel 1046 includes a microprocessor (not shown) and may be of any of the configuration depicted in FIGS. 7A-F.

In FIGS. 8-10, the reservoirs 804, 904a&b, and 1004a-c may be replaced by container receptacles containing different fluids. In such embodiments, the caps 806, 906a&b, and 1006a-c would include dip tubes as shown above and the conduits 816, 916a&b, and 1016a-c would extend from the dip tubes to the flow controllers 814, 914a&b, and 1014a-c.

Apparatus with Two Reservoirs

Figure 11:
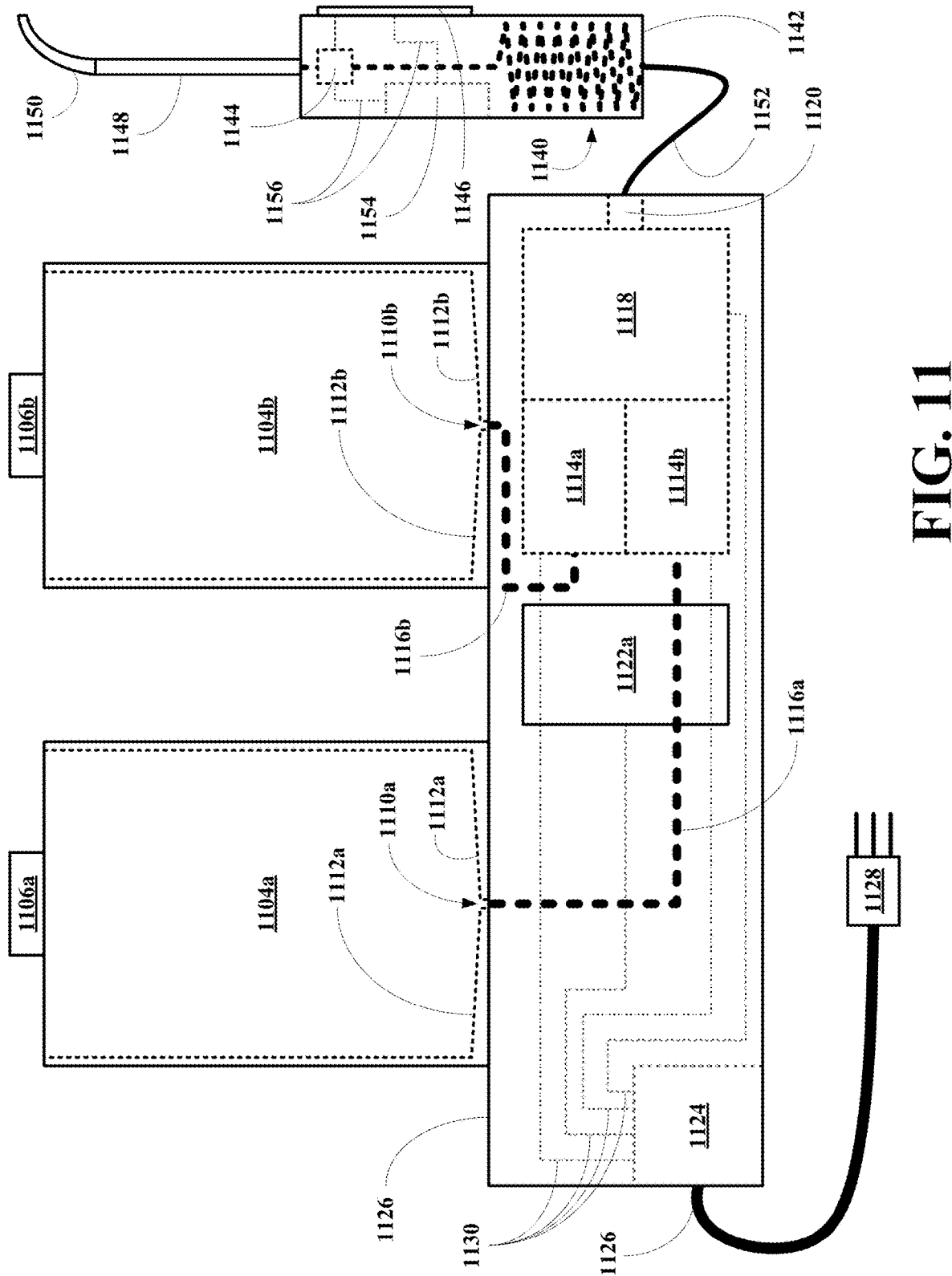
FIG. 11 depicts another embodiment of a fluid dispensing apparatus of this disclosure, where the apparatus includes three fluid reservoir, a wand, a pump, flow meters, a microprocessor, and a power supply.

Referring now to FIG. 11, another embodiment of dispensing apparatus of this disclosure, generally 1100, is shown to include a housing 1102, two fluid reservoirs 1104a&b including caps 1106a&b, fluid outlets 1110a&b, and drainage ramps 1112a-c. The apparatus 1100 also includes two flow controllers 1114a&b connected to the fluid outlets 1110a&b via fluid conduit 1116a&b. The flow controllers 1114a&b are in fluid communication with a pump 1118 having an outlet 1120. The apparatus 1100 also includes a control panel 1122 and a power supply 1124 having a power cord 1126 having a plug 1128. The power supply 1124 is connected to the panel 1122, the flow controllers 1114a&b and the pump 1118 via wires 1130. The control panel 1122 includes a microprocessor (not shown) and may be of any of the configuration depicted in FIGS. 7A-F.

The apparatus 1100 also includes a handheld fluid dispensing device or wand 1140 including a wand housing 1142 containing a control valve 1144, a wand control panel 1146, and a dispensing conduit 1148 having a nozzle 1150. The control valve 1144 is connected to the outlet 1120 of the pump 1118 via a flexible fluid conduit 1152. The wand 1140 also includes a power supply 1154. The power supply 1154 is connected to the wand panel 1146 and the control valve 1144 via wires 1156. The wand control panel 1146 includes a microprocessor (not shown) and may be of any of the configuration depicted in FIGS. 7A-F.

Apparatus with a Single Reservoir and a Pipette

Referring now to FIGS. 12A&B, another embodiment of dispensing apparatus of this disclosure, generally 1200, is shown to include a fluid reservoir 1202 including a cap 1204, wherein the cap 1204 is specially designed to work with an electronic pipette 1206 having a body 1208 and a pipette inlet/outlet 1210.

Apparatus with a Single Reservoir

Referring now to FIG. 13, another embodiment of a fluid dispensing apparatus of this disclosure, generally 1300, is shown to include a fluid container 1302 including a cap 1304 having a dip tube 1306 including a fluid inlet 1308 with radial slits 1310, a handle 1312, and a ramp 1314 as shown in the cutout area 1316.

The apparatus 1300 also includes a fluid dispensing device or wand 1320 including a fluid inlet connector 1322, an inlet fluid conduit 1324, a pump 1326, an outlet 1328, and an outlet fluid conduit 1330. The inlet fluid conduit 1324 connects the dip let 1306 to the pump 1326. The outlet fluid conduit 1332 connects that outlet 1328 to the pump 1326. The wand 1320 also includes a battery based power supply 1334 with batteries 1336, a microprocessor 1338, and a dispensing trigger 1340. The wand 1320 may also include a flow meter (not shown). The power supply 1334 supplies power to the microprocessor 1338, the pump 1326, the optional flow meter, and the trigger 1340 via electrical wires 1342. The microprocessor 1338 is in two-way communication via communication wires 1344 with the pump 1326, the optional flow meter, and the trigger 1340 and is configured to receive an output signal or signals from the trigger 1340, and to turn the pump 1326 ON or OFF. If the wand 1320 includes a flow meter to monitor fluid flow through the flow meter and to turn the pump 1326 OFF when the flow meter output indicates that a pre-defined or pre-set amount of fluid has passed through the flow meter. Of course, it should be recognized that the pump 1326 and flow meter may be integrated into a single metering pump. Additionally, the microprocessor 1338 is also configured to keep track of the amount of fluid dispensed and to notify a user when the fluid in the container containing the fluid is low and needs to be replaced and/or refilled. The apparatus 1300 also may includes a flexible fluid conduit as described above.

Apparatus with a Single Reservoir

Referring now to FIG. 14, another embodiment of a fluid dispensing apparatus of this disclosure, generally 1400, is shown to include a housing 1402 including a container receiving structure 1404 including an inlet connector 1406 having an inlet fluid conduit 1408 connect to a solenoid 1410 including an inlet connector 1412, and an outlet connector 1414. The housing 1402 also includes a solenoid outlet conduit 1416 connect to an housing fluid outlet connector 1418 terminating in a flexible conduit 1420. The housing 1402 also includes feet 1422 and an air grill 1424 and air flow channels 1426.

The housing 1402 also includes a fluid level sensor 1428 and a power supply 1430 having a power cord connector 1432 through which a power cord 1434 extends and having a plug 1436. The housing 1402 also includes a microprocessor 1438. The power supply 1430 provide power to the microprocessor 1438 and to the solenoid 1410 via wires 1440. The microprocessor 1438 is in two-way communication with the solenoid 1410 and the sensor 1428 via communication wires 1442.

The apparatus 1400 also includes a replaceable fluid container 1444 including a neck 1446 ending in an outlet connector 1448 having a fluid outlet 1450. The outlet connector 1448 and the fluid outlet 1450 are adapted to engage the inlet connector 1406 and the inlet fluid conduit 1408. The sensor 1428 supplies information to the microprocessor 1438 so that a user may be informed when the fluid level is low or the container 1444 is empty.

The apparatus 1400 also includes a handheld fluid dispensing device or wand 1460 connected to the flexible conduit 1420 and includes a battery pack 1462, a wand control panel 1464, and a dispensing outlet nozzle 1466. The housing also includes a wand bracket 1468 for storing the wand 1460 when it is not being used. The wand 1460 and the control panel 1464 may be any wand or control panel described therein. Of course, the wand 1460 may be connected to the power supply 1430 via a wire (not shown) attached to the flexible conduit 1420.

Apparatus with a Single Reservoir

Referring now to FIG. 15, another embodiment of a fluid dispensing apparatus of this disclosure, generally 1500, is shown to include a fluid container 1502 including a cap 1504, an inlet conduit 1506, an interior 1508, an outlet fluid conduit 1510 including a wire mesh fluid inlet 1512, a male outlet quick connector 1514 associated with the outlet fluid conduit 1510, a wand bracket 1516, and a ramp 1518.

The apparatus 1500 also includes a control unit 1550 having a control panel 1552 comprising a touchscreen. The control unit 1550 also includes a female inlet quick connector 1554, a inlet fluid conduit 1556, and a fluid outlet 1558 connected to a flexible fluid conduit 1560. The control unit 1550 also includes a microprocessor (not shown), a power supply (not shown), a pump (not shown) and may include a flow control (not shown), all of these components may be any of the components described in any of the embodiments therein. The apparatus 1500 also includes a handheld fluid dispensing device or wand 1562 including an fluid inlet connector 1564, a fluid outlet 1566, and a dispenser trigger 1568. The wand 1562 may also include any of the components of the wands described in any of the embodiments herein.

Apparatus with Two Single Reservoirs

Referring now to FIG. 16, another embodiment of a fluid dispensing apparatus of this disclosure, generally 1600, is shown to include a housing 1602 including two fluid container receiving members 1604a&b adapted to receive two fluid containers 1606a&b. The housing 1602 also includes a fluid outlet connector 1608, a flexible conduit bracket 1610, a flexible coiled fluid conduit 1612, a wand bracket 1614, a control panel 1616, and a plurality of control buttons 1618. The apparatus 1600 also includes a wand 1620 including a hanger 1622, a fluid inlet 1624, a fluid outlet 1626, a Start button, a 1 button, a 2 button, and a 3 button connected for starting fluid flow, select which fluid or a combination of both fluids; of course, the wand may be any wand described herein.

The apparatus 1600 may also include a microprocessor (not shown), a power supply (not shown), a pump (not shown) and flow controls (not shown), or any other components described in any of the embodiments therein. The wand 1620 may also include any of the components of the wands described in any of the embodiments herein.

Apparatus with Three Reservoirs

Figure 17B:
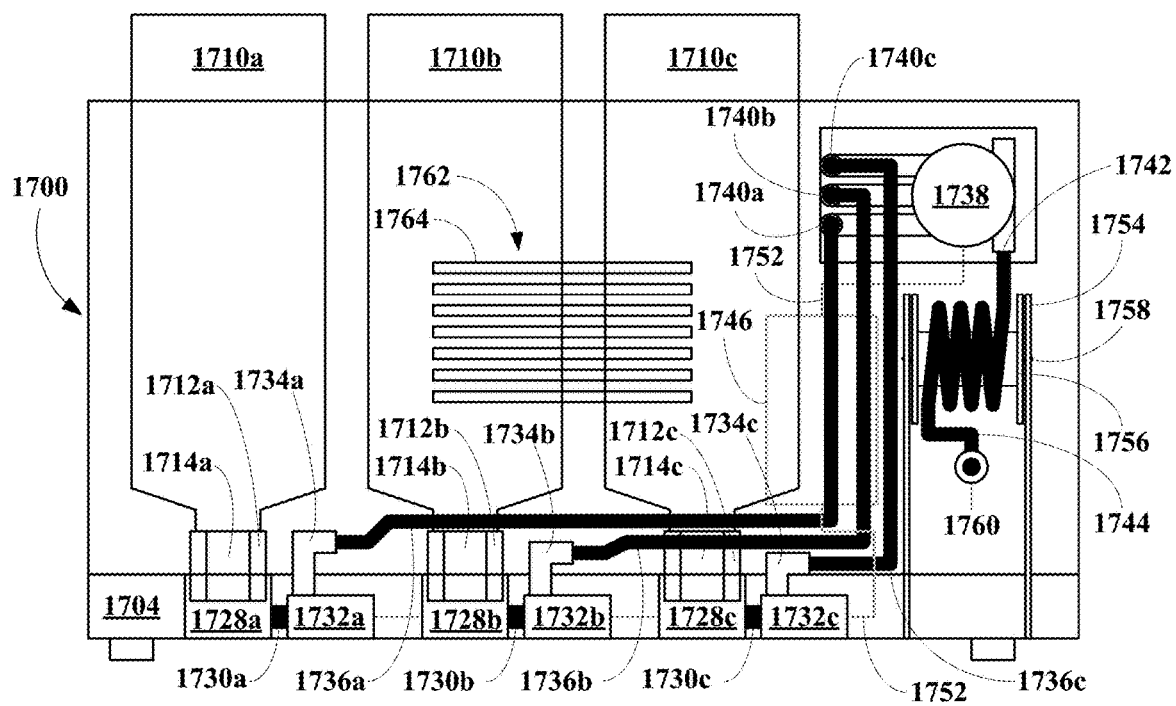

Referring now to FIGS. 17A&B, another embodiment of a fluid dispensing apparatus of this disclosure, generally 1700, is shown to include a removable housing 1702 and a stationary housing 1704 including feet 1706. The removable housing 1702 includes fluid sight windows or slots 1708a-c. The apparatus 1700 also includes three fluid containers 1710a-c including container fluid connectors 1712a-c having fluid outlet 1714a-c as shown in FIG. 17B, where the removable housing 1702 has been removed. The apparatus 1700 also include a wand receiving slot or area 1716 including a handheld wand 1718 positioned therein. The wand 1718 includes three selector buttons 1, 2, and 3 for selecting the fluid, a dispensing button 1720 and wireless communication hardware and associated software. The wand 1718 may also include a power supply such as batteries or a wire from a power supply in the apparatus 1700. The removable housing 1702 also include a control panel 1722 including an ON/OFF button 1724 and a support button 1726. The wand 1718 also includes a fluid inlet connector 1727.

The stationary housing 1704 includes three housing fluid connectors 1728a-c designed to receive the container connectors 1712a-c and including inlet conduits 1730a-c. The inlet conduits 1730a-c are connected to flow controllers 1732a-c including outlet fittings 1734a-c. The outlet fittings 1734a-c are connected to fluid conduits 1736a-c. The stationary housing 1704 includes a pump 1738 including pump inlets 1740a-c into which the conduits 1736a-c terminate and an outlet 1742 and an outlet conduit 1744. The apparatus 1700 also includes a control unit and power supply 1746 having a power cord 1748 having a plug 1750. The control unit/power supply 1746 is connected to the control panel 1722, the flow controllers 1732a-c and the pump 1738 via wires 1752. The control panel 1746 includes a microprocessor (not shown) and may be of any of the configuration described herein. The stationary housing 1704 also includes a bracket 1754 for a spool 1756 mounted on a shaft 1758 supported in the bracket 1754. The spool 1756 spools a length of the outlet conduit 1744. The stationary housing 1704 also includes an outlet fitting 1760. The outlet conduit 1744 is connected to the wand connector 1727. The stationary housing 1704 also include an air grill 1762 including air slits 1764.

Apparatus with Three Reservoirs

Referring now to FIGS. 18, another embodiment of a fluid dispensing apparatus of this disclosure, generally 1800, is shown to include a housing 1802 including a window 1804, an access door 1806 having a handle 1808 and three containers 1810a-c including outlet connectors 1812a-chaving fluid conduits 1814a-c. The housing 1802 also includes inlet flow controllers 1816a-c. The flow controllers 1816a-c are connected to a fluid conduit 1818. The apparatus 1800 also includes a solenoid or pump 1820 including a solenoid inlet 1822 connected to the conduit 1818, and a solenoid outlet 1824 connected to an outlet conduit 1826. The housing 1802 also includes a panel 1828 including a touchscreen 1830, a conduit fitting 1832 through which the conduit 1826 passes, and a wand receiver 1834 having a wand 1836 deposited therein. The wand 1836 includes an inlet connector 1838 to which the conduit 1826 connects. The apparatus 1800 also includes a power supply 1840 connected to a power cord 1842 having a plug 1844 and passing through a power fitting 1846. The apparatus 1800 also includes a controller 1848 having a microprocessor (not shown). The power supply 1840 supplies power to the solenoid 1820, the touchscreen 1830, and the flow controllers 1816a-c via power wires 1850. The controller 1848 is connected to the solenoid 1820, the touchscreen 1830, and the flow controllers 1816a-c via 2-way communication wires 1852.

Washing Machine with Three Container Fluid Dispenser

Referring now to FIG. 19, an embodiment of a washing machine apparatus, generally 1900, is shown to include a washing machine 1902 having a washing machine control panel 1904 for controlling the washing machine (controls not shown), a door 1906 having a handle 1908. The apparatus 1900 also includes a fluid dispensing unit 1910. The fluid dispensing unit 1910 includes a microprocessor 1912 and control buttons 1914, where the microprocessor 1912 and buttons 1914 are connected to the power supply of the washing machine (not shown). The unit 1910 also includes three fluid reservoirs 1916a-c and three covers 1918a-c having handles 1920a-c for opening the covers 1918a-c to add fluid into the reservoirs 1916a-c. The unit 1910 also includes conduits 1922a-cconnecting the reservoirs 1914a-c to fluid flow controllers 1924a-c, which may also include pumps, but because the reservoirs are above the flow controllers, gravity maybe sufficient to provide the needed pressure for adequate fluid flow. The controllers 1922a-c are connected to discharge conduits 1926a-c for discharging fluids into the interior of the washing machine 1902. The microprocessor 1912 controls the controllers 1924a-c and the buttons 1914 via communication wires 1928. It should be recognized that the microprocessor 1926 and the buttons 1928 may be integrated into the washing machine controls. The unit 1910 is designed to dispense laundry detergent, softener, or stain fluids or other fluids into the washing machine according to the buttons pushed. Of course, the buttons may be replaced by any controller described herein.

Distributed Washing Fluid Dispenser for Laundry Mats

Referring now to FIG. 20A, an embodiment of a laundry mat system of this disclosure, generally 2000, is shown to include a plurality of washing machines 2002a-l including doors 2004a-l having handles 2006a-l, control panels 2008a-l, and three different fluid inlets 2010a-l, 2012a-l, and 2014a-l. The system 2000 also includes a fluid dispensing unit 2020 including three different outlets 2022, 2024, and 2026 and three different fluid conduits 2028, 2030, and 2032.

Figure 20B:
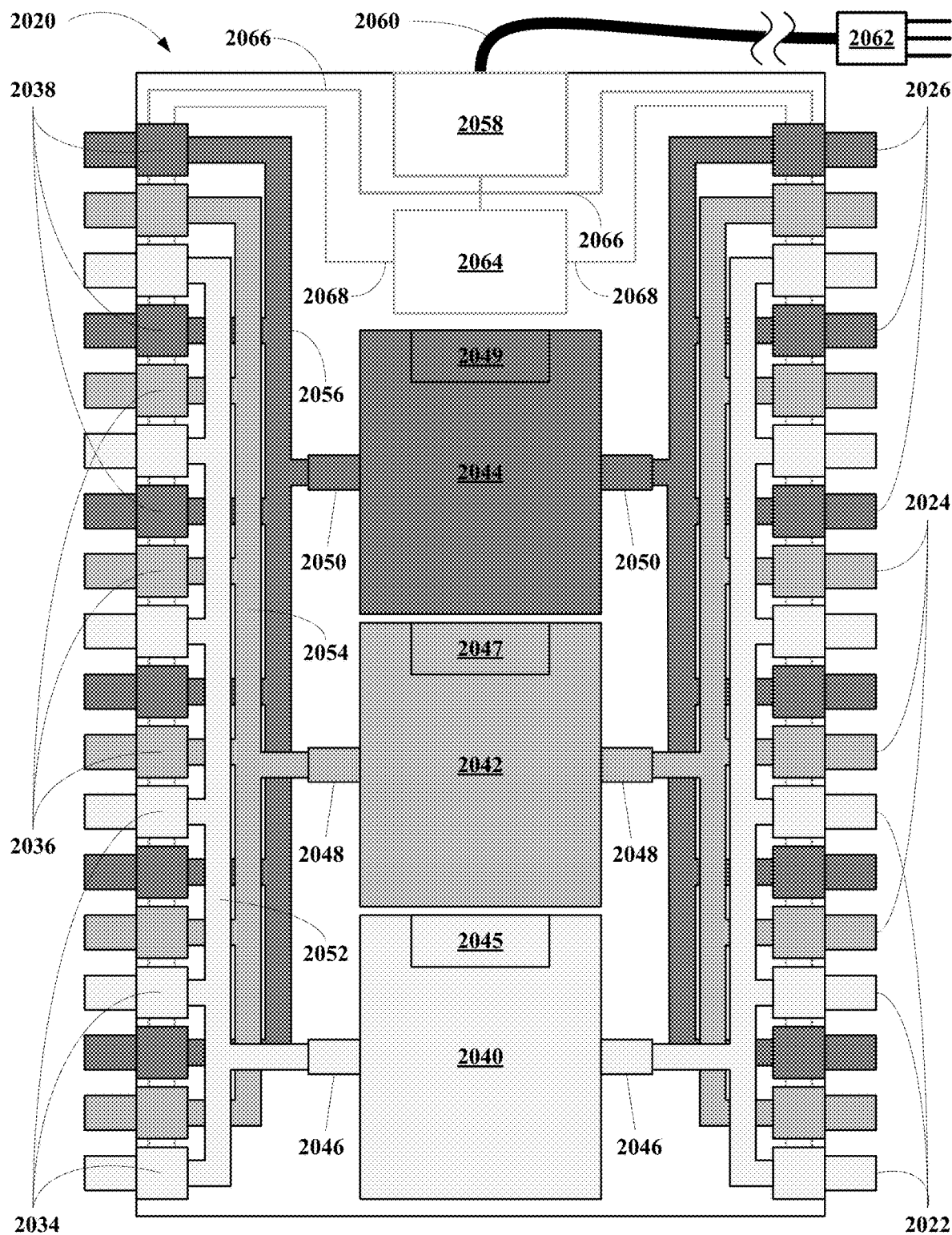

Referring now to FIG. 20B, the unit 2020 also includes three pump and fluid flow controllers 2034, 2036, and 2038 for controlling the fluid flow to the washing machines 2002a-l. The unit 2020 also include fluid reservoirs 2040, 2042, and 2044. The reservoir 2040 includes a refilling door 2045 and outlets 2046; the reservoir 2042 includes a refilling door 2047 and outlets 2048; and the reservoir 2044 includes a refilling door 2049 and outlets 2050. The unit 2020 includes conduits 2052, 2054, and 2056, where the conduit 2052 interconnects the reservoir 2040 to the pump/controllers 2034, the conduit 2054 interconnects the reservoir 2042 to the pump/controllers 2036, the reservoir 2044 to the pump/controllers 2038. The unit 2020 also includes a power supply 2058 including a cord 2060 having a plug 2062 and a processor 2064. The power supply 2058 supplies power to the pump/controllers 2034, 2036, and 2038 and the processor 2064 via power wires 2066. The processor 2064 controls the pump/controllers 2034, 2036, and 2038 via communication wires 2068. The processor 2064 is in wire less or wired communication with the washing machines 2002a-l.

When a user enters liquid commands via the washing machine control panels 2008a-l, the liquid commands are transmitted via the wireless communication or wired communication to the processor 2064 which issues instruction to the appropriate pump/controllers 2034, 2036, and 2038 to dispense the appropriate type and volume of fluid to the washing machines 2002a-l. Of course, each washing machine may be configured as shown in FIG. 19. All payments for use of the fluids may be affected via coin apparatuses well known in the art or via credit or debit card transactions or via automated account debiting. It should also be recognized that the apparatus of FIGS. 20A&B may include containers dedicated to specific detergents, softeners, or other laundry fluids, where the control panel of each washing machine may permit the consumer to select the type of laundry detergent, softener, and other fluid to be used.

Closing

All references cited herein are incorporated by reference. Although the disclosure has been disclosed with reference to its preferred embodiments, from reading this description those of skill in the art may appreciate changes and modification that may be made which do not depart from the scope and spirit of the disclosure as described above and claimed hereafter.

We claim:

1. A washing machine apparatus comprising:
a washing machine,
a washing machine control panel,
a laundry fluid dispensing apparatus including:
one or more fluid containers, each of the fluid containers includes:
a washing machine fluid,
a level sensor,
a container inlet, and
a container outlet;
one or more pumps, each of the one or more pumps includes:
a pump inlet adapted to engage one or more of the container outlets, and
a pump outlet adapted to dispense one or more washing machine fluids from
the one or more of the fluid containers, and
a control unit including:
a processing unit or a microprocessing unit having communication hardware and software,
at least one user feedback device,
at least one input device, and
one or more indicator lights, and
a power supply,
wherein:
the power supply is configured to supply power to the processing or microprocessing unit, the at least one user feedback device, the at least one input device, the one or more indicator lights, the one or more pumps, and the level sensors,
the processing or the microprocessing unit is configured to:
receive input from a user via the at least one input device comprising amount of and times for each of the one or more washing machine fluids to be dispensed,
turn on or off each of the one or more pumps to control the amount of each of the one or more washing machine fluids being dispensed from each of the fluid containers, and
turn on one of the indicator lights, when one of the level sensors indicates that
a fluid level in the containers drops below a low level threshold,
wherein the one or more washing machine fluids are selected from the group consisting of a laundry detergent fluid, a chlorine containing bleach fluid, a non-chlorine-containing bleach fluid, a fabric softener fluid, a stain removing fluid, a laundry pre-spotter fluid, concentrated versions thereof, and mixtures or combinations thereof.

2. The apparatus of claim 1, wherein the at least one input device and the at least one user feedback device comprise a touch screen including:
an ON/OFF selector, and
one or more washing machine fluid amount selectors.

3. The apparatus of claim 1, wherein the at least one input device includes:
an ON/OFF selector, and
one or more washing machine fluid amount selectors.

4. The apparatus of claim 1, wherein each of the one or more pumps comprises:
a metering pump.

5. The apparatus of claim 1, wherein the laundry fluid dispensing apparatus further comprises:
a mixing chamber adapted to mix together one or more washing machine fluids prior to dispensing the mixed fluid into the washing machine.

6. The apparatus of claim 5, wherein the mixing chamber includes:
a mixer.

7. A method for dispensing washing machine fluids comprising:
turning on a washing machine apparatus comprising:
a washing machine including one or more washing machine sensors,
a washing machine control panel,
a laundry fluid dispensing apparatus including:
one or more fluid containers, each of the fluid containers includes:
a washing machine fluid,
a level sensor,
a container inlet, and
a container outlet;

one or more pumps, each of the pumps includes:
a pump inlet adapted to engage one of the container outlets, and
a pump outlet adapted to dispense one or more washing machine
fluids from the one or more of the fluid containers into the washing machine, and
a processing unit or a microprocessing unit having communication hardware and software,
at least one user feedback device,
at least one input device, and
one or more indicator lights, and
a power supply configured to supply power to the processing or the microprocessing unit, the at least one user feedback unit, the at least one input device, the one or more indicator lights, the one or more pumps, and the level sensors,
receiving information from the washing machine sensors comprising amounts of and times for each of the one or more washing machine fluids to be dispensed,
turning on one or more of the one or more pumps via the processing unit or the microprocessing unit, and
dispensing the amount of and the time for each of the one or more washing machine fluids into the washing machine while the washing machine is running,
wherein the one or more washing machine fluids are selected from the group consisting of a laundry detergent fluid, a chlorine containing bleach fluid, a non-chlorine-containing bleach fluid, a fabric softener fluid, a stain removing fluid, a laundry pre-spotter fluid, concentrated versions thereof, and mixtures or combinations thereof.

8. The method of claim 7, wherein the information further comprising:
information from a website or a downloadable software application associated with each of the one or more washing machine fluids to set the amount of each of the one or more washing machine fluids to be dispensed to the washing machine.

* * * * *